United States Patent
Yoo et al.

(10) Patent No.: US 10,947,241 B2
(45) Date of Patent: Mar. 16, 2021

(54) PHENYL PHTHALAZINE DERIVATIVE, METHOD FOR THE PREPARATION THEREOF, AND PHARMACEUTICAL COMPOSITION COMPRISING THE SAME

(71) Applicant: Seoul National University Hospital, Seoul (KR)

(72) Inventors: Ja Kyung Yoo, Gyeonggi-do (KR); Nora Lee, Gyeonggi-do (KR); Chun Ho Lee, Seoul (KR); Myunggi Jung, Gyeonggi-do (KR); Hyo-Soo Kim, Seoul (KR)

(73) Assignee: Seoul National University Hospital, Seoul (KR)

( * ) Notice: Subject to any disclaimer, the term of this patent is extended or adjusted under 35 U.S.C. 154(b) by 0 days.

(21) Appl. No.: 16/344,080

(22) PCT Filed: Oct. 27, 2017

(86) PCT No.: PCT/KR2017/011964
§ 371 (c)(1),
(2) Date: Apr. 23, 2019

(87) PCT Pub. No.: WO2018/080216
PCT Pub. Date: May 3, 2018

(65) Prior Publication Data
US 2019/0241574 A1 Aug. 8, 2019

(30) Foreign Application Priority Data
Oct. 28, 2016 (KR) ........................ 10-2016-0141765

(51) Int. Cl.
| | | |
|---|---|---|
| *C07D 403/04* | (2006.01) | |
| *A61K 31/502* | (2006.01) | |
| *C07D 487/04* | (2006.01) | |
| *C07D 403/12* | (2006.01) | |
| *C07D 401/04* | (2006.01) | |
| *C07D 401/12* | (2006.01) | |
| *C07D 237/34* | (2006.01) | |
| *C07D 471/04* | (2006.01) | |
| *C07D 405/12* | (2006.01) | |
| *C07D 217/22* | (2006.01) | |
| *A61P 9/10* | (2006.01) | |
| *A61P 9/12* | (2006.01) | |
| *C07D 401/14* | (2006.01) | |
| *C07D 403/14* | (2006.01) | |
| *C07D 405/14* | (2006.01) |

(52) U.S. Cl.
CPC .............. *C07D 487/04* (2013.01); *A61P 9/10* (2018.01); *A61P 9/12* (2018.01); *C07D 217/22* (2013.01); *C07D 237/34* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 471/04* (2013.01)

(58) Field of Classification Search
CPC ... C07D 237/30; C07D 403/04; C07D 413/04
See application file for complete search history.

(56) References Cited

U.S. PATENT DOCUMENTS

| 3,753,988 A * | 8/1973 | Rodway et al. ..... C07D 237/34 544/237 |
|---|---|---|
| 8,338,591 B2 | 12/2012 | Yoon et al. |
| 2007/0099895 A1 | 5/2007 | Augereau et al. |

FOREIGN PATENT DOCUMENTS

| WO | WO-2007/118602 A1 | 10/2007 |
|---|---|---|
| WO | WO-2013/096820 A1 | 6/2013 |

OTHER PUBLICATIONS

CA Registry No. 304862-51-9, entered into CA Registry File on Nov. 29, 2000, supplied by OTAVA Chemicals. by Auro,a FineChemica ls.*
OTAVA Product Guide, 1 page retrieved from the Internet at https://otavachemicals.com/component/search/?searchword=Search+the+web-site&ordering=&searchphrase=all on Apr. 3, 2020.*
Lee et al., "Adenylyl Cyclase-Associated Protein 1 is a Receptor for Human Resistin and Mediates Inflammatory Actions of Human Monocytes", Cell Metabolism 19, Mar. 4, 2014, pp. 484-497.
Park et al., "Resistin in Rodents and Humans", Diabetes & Metabolism Journal, 37, 2013, pp. 404-414.

(Continued)

*Primary Examiner* — Emily A Bernhardt
(74) *Attorney, Agent, or Firm* — Marshall, Gerstein & Borun LLP

(57) ABSTRACT

The present invention relates to a compound represented by Chemical Formula 1, or a pharmaceutically acceptable salt thereof. The compound according to the present invention can be usefully used for the prevention or treatment of cardiovascular diseases.

[Chemical Formula 1]

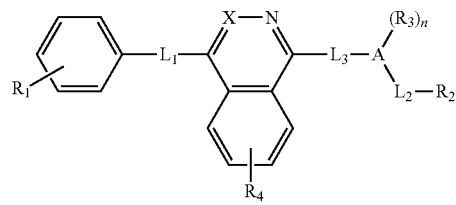

6 Claims, No Drawings

(56) References Cited

OTHER PUBLICATIONS

Ouchi et al., "Adipokines in Inflammation and Metabolic Disease", Nature Reviews, Immunology, vol. 11, Feb. 2011, pp. 85-97.
Steppan et al., "The Hormone Resistin Links Obesity to Diabetes", Nature, vol. 409, Jan. 18, 2001, pp. 307-312.
Patel et al., "Disulfide-Dependent Multimeric Assembly of Resistin Family Hormones", Science, vol. 304, May 21, 2004, pp. 1154-1158.
Search Report and Written Opinion in International Application No. PCT/KR2017/011964 dated Feb. 7, 2018, 13 pages.

* cited by examiner

PHENYL PHTHALAZINE DERIVATIVE, METHOD FOR THE PREPARATION THEREOF, AND PHARMACEUTICAL COMPOSITION COMPRISING THE SAME

TECHNICAL FIELD

The present invention relates to a novel phenyl phthalazine derivative which can be usefully used for the prevention or treatment of cardiovascular diseases, a method for the preparation thereof and a pharmaceutical composition comprising the same.

BACKGROUND OF ART

Recently, as adipokine, a hormone secreted by fat, is known to play an important role in the occurrence of obesity-related complications in addition to known hematologic and metabolic factors, it is expected to be able to prevent or treat related diseases by adjusting its actions.

The importance of adipokine has been proven that severe insulin resistance, hyperglycemia, hyperlipidemia, fatty liver and the like have been found in animal models or humans having a congenital deficiency of adipose tissue. Representative types of the adipokines which have been known to date include leptin, adiponectin, TNF-alpha, Resistin, interleukin-6, plasminogen activator inhibitor-1, TGF-beta and the like (Nat Rev Immunol, 2011, 11(2), 85-97). Resistin was first discovered as a substance that mediates insulin resistance in obese mice.

Rodent resistin is secreted from adipocytes, which is presumed to be associated with obesity-related insulin resistance and type 2 diabetes (Nature, 2001, 409, 307-312). However, human resistin is quite different from rodent resistin. Human resistin is a cytokine that is secreted from monocytes and induces chronic inflammations. These chronic inflammations can lead to diabetes, obesity, liver disease, arteriosclerosis, rheumatoid arthritis and other cardiovascular diseases (Diabetes Metab J, 2013, 37, 404-414).

Resistin is a small protein of 12.5 KDa, and six monomers are linked to each other to form a hexamer (Science 2004, 304, 1154-1158). In a recent research, it was first discovered in the world that the receptor for human resistin is CAP1. Resistin increases cAMP via CAP1 and induces the expression of inflammatory cytokines via PKA, NFkB signaling system. Further, the research has reported that human resistin directly binds to CAP1 in monocytes, and involves in cAMP concentration, PKA activity and NF-kappaB-related transcription of inflammatory cytokines, and over-expression of CAP1 enhanced resistin-induced increased activity of cAMP-dependent signaling pathway. In particular, the transgenic mouse model has been shown that CAP1-overexpressed monocytes aggravated adipose tissue inflammation in transgenic mice. In contrast, it has been shown that inhibition of CAP1 expression abrogated the resistin-mediated inflammatory activity both in vitro and in vivo (Cell Metab, 2014, 19(3), 484-497).

Therefore, by developing a drug that effectively adjusts the action of resistin and CAP1, it is expected to be able to prevent and treat related diseases, especially cardiovascular diseases.

DETAILED DESCRIPTION OF THE INVENTION

Technical Problem

It is one object of the present invention to provide a novel phenyl phthalazine derivative which can be usefully used for the prevention or treatment of cardiovascular diseases, and a method for the preparation thereof.

It is another object of the present invention to provide a pharmaceutical composition comprising the phenyl phthalazine derivative.

Technical Solution

In order to achieve the above objects, the present invention provides a compound represented by the following Chemical Formula 1, or a pharmaceutically acceptable salt thereof:

[Chemical Formula 1]

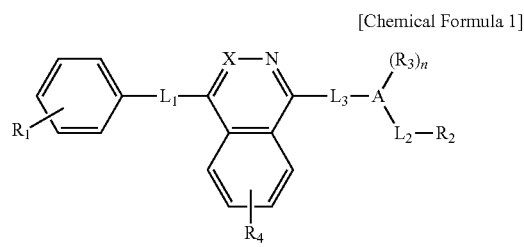

in Chemical Formula 1,

X is CH, or N, $L_1$ is a single bond, $C_{1-4}$ alkylene, $C_{2-4}$ alkenylene, NH, O, or $SO_2$, $L_2$ is a single bond, $C_{1-4}$ alkylene, —O—($C_{1-4}$ alkylene)-, —($C_{1-4}$ alkylene)-O—, CO, NH, NHCO, O, OCO, $SO_2$, or $COCHNH_2$, $L_3$ is a single bond, or —O—, A is N, or a 5- to 9-membered heterocycloalkane ring or heterobicycloalkane ring containing one or two nitrogen atoms, $R_1$ is hydrogen, $C_{1-4}$ alkyl, $C_{1-4}$ alkyl substituted with carboxy group, $C_{1-4}$ haloalkyl, $C_{1-4}$ alkoxy, $C_{1-4}$ haloalkoxy, halogen, cyano, nitro, 4-methylpiperazin-1-carbonyl, carboxy, morpholino, ($C_{1-4}$ alkyl)sulfonyl, (piperidinyl)sulfonyl, or (piperazinyl)sulfonyl, $R_2$ is $C_{1-5}$ alkyl unsubstituted or substituted with amino, carboxy, —COO($C_{1-4}$ alkyl), —CONH$_2$, benzyloxy, or imidazole; $C_{3-6}$ cycloalkyl unsubstituted or substituted with amino; amino; NH($C_{1-4}$ alkyl); N(CO$_{1-4}$ alkyl)$_2$; hydroxy; carboxy; —COO($C_{1-4}$ alkyl); phenyl; or a 5- or 6-membered heterocyclic group containing 1 to 3 heteroatoms each independently selected from the group consisting of N, O and S, $R_3$ is hydrogen, or $C_{1-4}$ alkyl, $R_4$ is hydrogen, or halogen, and n is 1 or 2, provided that when A is N, n is 1.

Preferably, $L_1$ is a single bond, —CH$_2$—, —CH=CH—, —CH$_2$—CH=CH—, NH, O, or $SO_2$.

Preferably, $L_2$ is a single bond, —CH$_2$—, —CH$_2$CH$_2$—, —CH$_2$CH$_2$CH$_2$—, —O—(CH$_2$)—, —(CH$_2$CH$_2$)—O—, CO, NH, NHCO, O, OCO, $SO_2$, or $COCHNH_2$.

Preferably, $R_1$ is hydrogen, methyl, ethyl substituted with carboxy group, trifluoromethyl, methoxy, trifluoromethoxy, fluoro, chloro, cyano, nitro, 4-methylpiperazine-1-carbonyl, carboxy, morpholino, methylsulfonyl, (piperidin-1-yl)sulfonyl, or (piperazin-1-yl)sulfonyl, Preferably, $R_2$ is methyl, ethyl, propyl, isopropyl, butyl, isobutyl, pentyl, or isopentyl, unsubstituted or substituted with amino, carboxy, —COO(ethyl), —CONH$_2$, benzyloxy, or imidazole; cyclopropyl, cyclobutyl, or cyclopentyl, unsubstituted or substituted with amino; amino; methylamino; dimethylamino; hydroxy; carboxy; —COO(ethyl); phenyl; morpholino; pyrrolidinyl; tetrahydro-2H-pyranyl; or pyridine.

Preferably, A is any one ring selected from the group consisting of pyrrolidine, piperazine, piperidine, 1,2,3,5-tetrahydropyridine, 1,4-diazepan, octahydro-IH-pyrrolo[2,3-c]pyridine, and octahydropyrrolo[3,4-b] pyrrolo.

Preferably, A is any one of the following:

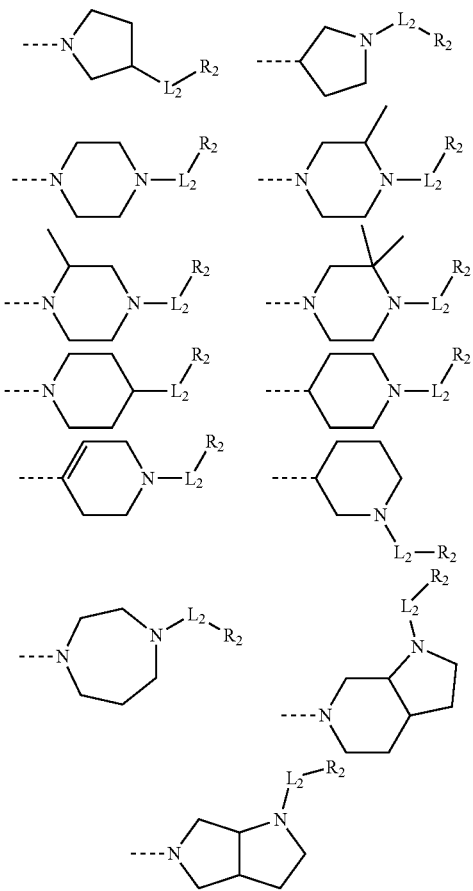

Preferably, $L_3$ is a single bond, and A is represented by the following formula 1':

[Chemical Formula 1']

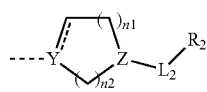

in Chemical Formula 1',

Y is N, ∥ is a single bond, or Y is C, and ∥ is a double bond,
Z is CH, or N,
n1 is 1 or 2,
n2 is 1, 2 or 3.
Preferably, n1 is 1, n2 is 1, 2 or 3; or n1 is 2, and n2 is 3.

Preferably, Y is N ∥ is a single bond, and Z is N.
Preferably,
X is N,
$L_1$ is a single bond, $L_2$ is a single bond, $C_{1-4}$ alkylene, —($C_{1-4}$ alkylene)-O—, CO, NH, NHCO, or $SO_2$,
$R_1$ is hydrogen, $C_{1-4}$ alkyl, or halogen,
$R_2$ is $C_{1-4}$ alkyl unsubstituted or substituted with amino; $C_{3-6}$ cycloalkyl; amino; $N(C_{1-4}$ alkyl$)_2$; hydroxy; morpholino; or pyrrolidinyl,
n1 is 1, and
n2 is 1, or 2.

Representative examples of the compound represented by the Chemical Formula 1 are as follows:
1) 2-(4-(4-phenylphthalazin-1-yl)piperazin-1-yl)ethanol,
2) 1-(4-(4-p-tolylphthalazin-1-yl)piperazin-1-yl)ethanone,
3) 1-(4-methyl-1,4-diazepan-1-yl)-4-phenylphthalazine,
4) 2-(1-(4-(4-chlorophenyl)phthalazin-1-yl)piperidin-4-yl) ethanol,
5) 2-(4-(4-(4-chlorophenyl)phthalazin-1-yl)piperazin-1-yl)-N,N-dimethylethanamine,
6) 1-(4-chlorophenyl)-4-(4-(pyridin-2-yl)piperazin-1-yl) phthalazine,
7) 1-(4-chlorophenyl)-4-(4-(pyrrolidin-1-yl)piperidin-1-yl) phthalazine,
8) 4-(1-(4-(4-chlorophenyl)phthalazin-1-yl)piperidin-4-yl) morpholine,
9) 1-(4-chlorophenyl)-4-(4-(2-methoxyethyl)piperazin-1-yl) phthalazine,
10) (4-(4-(4-chlorophenyl)phthalazin-1-yl)piperazin-1-yl) (cyclopropyl)methanone,
11) 2-(1-(6-(4-chlorophenyl)pyridazin-3-yl)piperidin-4-yl) ethanol,
12) cyclopropyl(4-(4-(4-fluorophenyl)phthalazin-1-yl)piperazin-1-yl)methanone,
13) cyclopropyl(4-(4-(2-fluorophenyl)phthalazin-1-yl)piperazin-1-yl)methanone,
14) cyclopropyl(4-(4-(3-fluorophenyl)phthalazin-1-yl)piperazin-1-yl)methanone,
15) (4-(4-(3-chlorophenyl)phthalazin-1-yl)piperazin-1-yl) (cyclopropyl)methanone,
16) cyclopropyl(4-(4-(4-methoxyphenyl)phthalazin-1-yl) piperazin-1-yl)methanone,
17) 4-(4-(4-(cyclopropanecarbonyl)piperazin-1-yl)phthalazin-1-yl)benzonitrile,
18) cyclopropyl(4-(4-(4-nitrophenyl)phthalazin-1-yl)piperazin-1-yl)methanone,
19) cyclopropyl(4-(4-(2-fluoro-4-methoxyphenyl)phthalazin-1-yl)piperazin-1-yl)methanone,
20) cyclopropyl(4-(4-phenylisoquinolin-1-yl)piperazin-1-yl)methanone,
21) cyclopropyl(4-(4-(4-fluorophenyl)isoquinolin-1-yl)piperazin-1-yl)methanone,
22) (4-(4-(4-chlorophenyl)isoquinolin-1-yl)piperazin-1-yl) (cyclopropyl)methanone,
23) cyclopropyl(4-(4-(4-methoxyphenyl)isoquinolin-1-yl) piperazin-1-yl)methanone,
24) (E)-(4-(4-(4-chlorostyryl)phthalazin-1-yl)piperazin-1-yl)(cyclopropyl)methanone,
25) (E)-(4-(4-(4-chlorostyryl)isoquinolin-1-yl)piperazin-1-yl)(cyclopropyl)methanone,
26) (E)-cyclopropyl(4-(4-styrylisoquinolin-1-yl)piperazin-1-yl)methanone,
27) (E)-cyclopropyl(4-(4-(3-phenylprop-1-enyl)phthalazin-1-yl)piperazin-1-yl)methanone,
28) (E)-cyclopropyl(4-(4-(3-phenylprop-1-enyl)isoquinolin-1-yl)piperazin-1-yl)methanone,
29) (4-(4-(4-chlorophenyl)phthalazin-1-yl)-1,4-diazepan-1-yl)(cyclopropyl)methanone,
30) 1-(4-chlorophenyl)-4-(4-(2-methoxyethyl)-1,4-diazepan-1-yl)phthalazine, 31) 2-amino-1-(4-(4-(4-chlorophenyl)phthalazin-1-yl)piperazin-1-yl)ethanone hydrochloride,
32) 1-(4-chlorophenyl)-4-(4-(methylsulfonyl)piperazin-1-yl)phthalazine,
33) 1-(4-chlorophenyl)-4-(4-(tetrahydro-2H-pyran-4-ylsulfonyl)piperazin-1-yl)phthalazine,
34) 1-(4-chlorophenyl)-4-(4-(cyclopentylsulfonyl)piperazin-1-yl)phthalazine,
35) (1-aminocyclobutyl)(4-(4-(4-chlorophenyl)phthalazin-1-yl)piperazin-1-yl)methanone hydrochloride,
36) (R)-2-amino-1-(4-(4-(4-chlorophenyl)phthalazin-1-yl)piperazin-1-yl)propan-1-one hydrochloride,
37) 1-(4-chlorophenyl)-4-(4-(cyclopropylsulfonyl)piperazin-1-yl)phthalazine,
38) 2-(4-(4-(4-chlorophenyl)phthalazin-1-yl)piperazin-1-yl)ethanamine hydrochloride,
39) 1-(4-chlorophenyl)-4-(4-methoxypiperidin-1-yl)phthalazine,
40) 1-(4-chlorophenyl)-4-(4-ethoxypiperidin-1-yl)phthalazine,
41) 1-(4-chlorophenyl)-4-(4-(cyclopropylmethoxy)piperidin-1-yl)phthalazine,
42) 1-(4-(4-chlorophenyl)phthalazin-1-yl)piperidin-4-yl cyclopropanecarboxylate,
43) 2-amino-1-(4-(4-(4-chlorophenyl)phthalazin-1-yl)piperazin-1-yl)-2-methylpropan-1-one hydrochloride,
44) 2-amino-1-(4-(4-(4-chlorophenyl)phthalazin-1-yl)-5,6-dihydropyridin-1(2H)-yl)-2-methylpropan-1-one hydrochloride,
45) N-(1-(4-(4-chlorophenyl)phthalazin-1-yl)pyrrolidin-3-yl)acetamide,
46) 1-(4-(4-chlorophenyl)phthalazin-1-yl)-N-methylpyrrolidin-3-amine hydrochloride,
47) (S)-2-amino-1-(4-(4-(4-chlorophenyl)phthalazin-1-yl)piperazin-1-yl)-3-methylbutan-1-one,
48) (4-(4-(4-chlorophenyl)phthalazin-1-yl)-5,6-dihydropyridin-1(2H)-yl)(cyclopropyl)methanone,
49) 1-(4-chlorophenyl)-4-(1-(cyclopropylsulfonyl)-1,2,3,6-tetrahydropyridin-4-yl)phthalazine,
50) 1-(4-chlorophenyl)-4-(4-(cyclopropylmethyl)piperazin-1-yl)phthalazine,
51) (R)-(4-(4-(4-chlorophenyl)phthalazin-1-yl)piperazin-1-yl)(pyrrolidin-2-yl)methanone,
52) (1-aminocyclopropyl)(4-(4-(4-chlorophenyl)phthalazin-1-yl)piperazin-1-yl)methanone,
53) N1-(4-(4-chlorophenyl)phthalazin-1-yl)-N1,N2-dimethylethane-1,2-diamine,
54) 1-(4-(4-chlorophenyl)phthalazin-1-yl)-N-ethylpyrrolidin-3-amine,
55) N1-(4-(4-chlorophenyl)phthalazin-1-yl)-N1,N3-dimethylpropane-1,3-diamine,
56) (4-(4-(4-chlorophenyl)phthalazin-1-yl)piperidin-1-yl)(cyclopropyl)methanone,
57) (R)-1-(4-(4-chlorophenyl)phthalazin-1-yl)-N-methylpiperidin-3-amine,
58) (1-aminocyclopentyl)(4-(4-(4-chlorophenyl)phthalazin-1-yl)piperazin-1-yl)methanone,
59) (S)-(4-(4-(4-chlorophenyl)phthalazin-1-yl)piperazin-1-yl)(pyrrolidin-2-yl)methanone,
60) (2S,3S)-2-amino-1-(4-(4-(4-chlorophenyl)phthalazin-1-yl)piperazin-1-yl)-3-methylpentan-1-one,
61) (S)-2-amino-1-(4-(4-(4-chlorophenyl)phthalazin-1-yl)piperidin-1-yl)-3-methylbutan-1-one,
62) (S)-(4-(4-(4-chlorophenyl)phthalazin-1-yl)piperidin-1-yl)(pyrrolidin-2-yl)methanone,
63) (2S,3S)-2-amino-1-(4-(4-(4-chlorophenyl)phthalazin-1-yl)piperidin-1-yl)-3-methylpentan-1-one,
64) 2-amino-1-(4-(4-(4-chlorophenyl)phthalazin-1-yl)piperidin-1-yl)-2-methylpropan-1-one,
65) ethyl 2-(4-(4-(4-chlorophenyl)phthalazin-1-yl)piperazin-1-yl)acetate,
66) ethyl 2-(4-(4-(4-chlorophenyl)phthalazin-1-yl)piperazin-1-yl)-2-methylpropanoate,
67) 1-(4-benzyl-1,4-diazepan-1-yl)-4-(4-chlorophenyl)phthalazine,
68) 2-(4-(4-(4-chlorophenyl)phthalazin-1-yl)piperazin-1-yl)acetic acid,
69) (S)-2-amino-1-(4-(4-(4-chlorophenyl)phthalazin-1-yl)-2,2-dimethylpiperazin-1-yl)-3-methylbutan-1-one,
70) (R)-2-amino-1-(4-(4-(4-chlorophenyl)phthalazin-1-yl)-2-methylpiperazin-1-yl)-2-methylpropan-1-one,
71) (S)-2-amino-1-((R)-4-(4-(4-chlorophenyl)phthalazin-1-yl)-2-methylpiperazin-1-yl)-3-methylbutan-1-one,
72) (S)-2-amino-1-(4-(4-(4-chlorophenyl)phthalazin-1-yl)-2-methylpiperazin-1-yl)-2-methylpropan-1-one,
73) (S)-2-amino-1-((S)-4-(4-(4-chlorophenyl)phthalazin-1-yl)-2-methylpiperazin-1-yl)-3-methylbutan-1-one,
74) (S)-2-amino-1-(4-(4-(4-chlorophenyl)phthalazin-1-yl)-3-methylpiperazin-1-yl)-2-methylpropan-1-one,
75) (S)-2-amino-1-((S)-4-(4-(4-chlorophenyl)phthalazin-1-yl)-3-methylpiperazin-1-yl)-3-methylbutan-1-one,
76) (S)-2-amino-1-(4-(4-(4-chlorophenyl)phthalazin-1-yl)piperazin-1-yl)-3-(1H-imidazol-4-yl)propan-1-one,
77) 2-amino-1-(4-(4-(4-chlorophenyl)phthalazin-1-yl)piperazin-1-yl)-3,3-dimethylbutan-1-one,
78) (4-(4-(4-chlorophenyl)phthalazin-1-yl)piperazin-1-yl)(piperidin-2-yl)methanone,
79) (S)-2-amino-3-(benzyloxy)-1-(4-(4-(4-chlorophenyl)phthalazin-1-yl)piperazin-1-yl)propan-1-one,
80) (S)-2-amino-1-(4-(4-(4-chlorophenyl)phthalazin-1-yl)piperazin-1-yl)-2-phenylethanone,
81) (S)-5-(4-(4-(4-chlorophenyl)phthalazin-1-yl)piperazine-1-carbonyl)piperazin-2-one,
82) 2-(4-(4-(4-chlorophenyl)phthalazin-1-yl)piperazin-1-yl)-2-methylpropanoic acid,
83) 3-amino-4-(4-(4-(4-chlorophenyl)phthalazin-1-yl)piperazin-1-yl)-4-oxobutanoic acid,
84) 4-amino-5-(4-(4-(4-chlorophenyl)phthalazin-1-yl)piperazin-1-yl)-5-oxopentanamide,
85) 3-amino-4-(4-(4-(4-chlorophenyl)phthalazin-1-yl)piperazin-1-yl)-4-oxobutanamide,
86) 4-amino-5-(4-(4-(4-chlorophenyl)phthalazin-1-yl)piperazin-1-yl)-5-oxopentanoic acid,
87) 1-(4-chlorophenyl)-4-(tetrahydro-1H-pyrrolo[2,3-c]pyridin-6(2H,7H,7aH)-yl)phthalazine,
88) 1-(4-chlorophenyl)-4-(hexahydropyrrolo[3,4-b]pyrrol-5(1H)-yl)phthalazine,
89) 1-(7-chloro-4-(4-chlorophenyl)phthalazin-1-yl)-N-methylpyrrolidin-3-amine,
90) 1-(6-chloro-4-(4-chlorophenyl)phthalazin-1-yl)-N-methylpyrrolidin-3-amine,
91) 1-(4-(4-chlorophenyl)-6-fluorophthalazin-1-yl)-N-methylpyrrolidin-3-amine,
92) 1-(4-(4-chlorophenylsulfonyl)phthalazin-1-yl)-N-methylpyrrolidin-3-amine,
93) 1-(4-(4-chlorophenoxy)phthalazin-1-yl)-N-methylpyrrolidin-3-amine,
94) 2-amino-1-(4-(4-(4-chlorophenoxy)phthalazin-1-yl)piperazin-1-yl)-2-methylpropan-1-one,
95) (S)-1-(4-chlorophenyl)-4-(pyrrolidin-3-yloxy)phthalazine,
96) 1-(4-chlorophenyl)-4-(piperidin-3-yloxy)phthalazine,
97) N-(4-chlorophenyl)-4-(3-(methylamino)pyrrolidin-1-yl)phthalazin-1-amine, 98) 1-(4-(4-chlorobenzyl)phthalazin-1-yl)-N-methylpyrrolidin-3-amine,
99) 3-(4-(4-(2-amino-2-methylpropanoyl)piperazin-1-yl)phthalazin-1-yl)benzoic acid,
100) 2-amino-2-methyl-1-(4-(4-(4-morpholinophenyl)phthalazin-1-yl)piperazin-1-yl)propan-1-one,
101) 2-amino-2-methyl-1-(4-(4-(4-(methylsulfonyl)phenyl)phthalazin-1-yl)piperazin-1-yl)propan-1-one,
102) 2-amino-2-methyl-1-(4-(4-(4-(trifluoromethyl)phenyl)phthalazin-1-yl)piperazin-1-yl)propan-1-one,
103) 2-amino-2-methyl-1-(4-(4-(4-(trifluoromethoxy)phenyl)phthalazin-1-yl)piperazin-1-yl)propan-1-one,
104) 3-(4-(4-(4-(2-amino-2-methylpropanoyl)piperazin-1-yl)phthalazin-1-yl)phenyl)propanoic acid,
105) 4-(4-(4-(2-amino-2-methylpropanoyl)piperazin-1-yl)phthalazin-1-yl)benzoic acid,
106) 2-amino-2-methyl-1-(4-(4-(4-(4-methylpiperazine-1-carbonyl)phenyl)phthalazin-1-yl)piperazin-1-yl)propan-1-one,
107) 2-amino-2-methyl-1-(4-(4-(4-(piperidin-1-ylsulfonyl)phenyl)phthalazin-1-yl)piperazin-1-yl)propan-1-one, and
108) 2-amino-2-methyl-1-(4-(4-(3-(piperazin-1-ylsulfonyl)phenyl)phthalazin-1-yl)piperazin-1-yl)propan-1-one.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto.

In addition, a pharmaceutically acceptable metal salt can be obtained by a conventional method using a base. For example, a compound represented by Chemical Formula 1 is dissolved in an excessive amount of an alkali metal hydroxide or an alkaline earth metal hydroxide solution, the non-soluble salt is filtered, and the filtrate is evaporated and dried to obtain a pharmaceutically acceptable metal salt. At this time, it is particularly preferable to prepare a sodium salt, a potassium salt or a calcium salt as the metal salt.

A pharmaceutically unacceptable salt or solvate of the compound of Chemical Formula 1 may be used as an intermediate when preparing the compound of Chemical Formula 1, or the pharmaceutically acceptable salt or the solvate thereof.

Further, the compound of Chemical Formula 1 according to the present invention includes not only pharmaceutically acceptable salts thereof, but also solvates such as hydrates that can be prepared therefrom, and includes all possible stereoisomers, but are not limited thereto. The solvate and the stereoisomer of the compound of Chemical Formula 1 may be prepared from the compound of Chemical Formula 1 using common methods known in the art.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

In addition, the present invention can produce, for example, the compound represented by Chemical Formula 1 by a preparation method as shown in Reaction Scheme 1 below.

[Reaction Scheme 1]

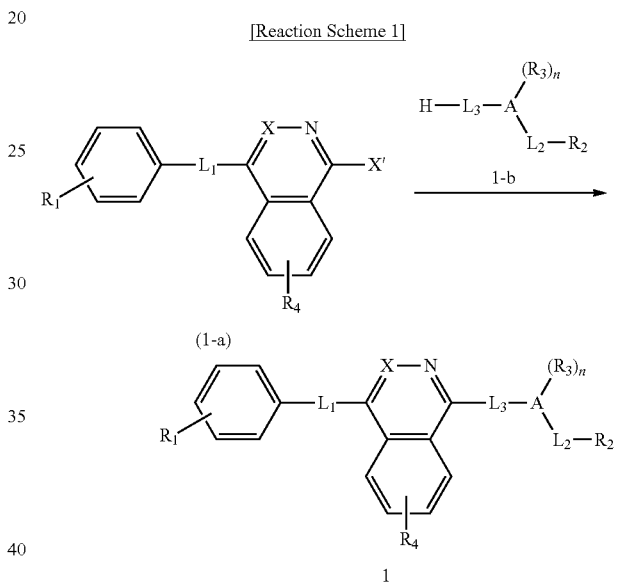

In Reaction Scheme 1, X, $L_1$, $L_2$, $L_3$, A, $R_1$, $R_2$, $R_3$, $R_4$ and n are as defined above and X' is halogen. More preferably, X' is chloro.

The reaction is carried out preferably in the presence of triethylamine. In addition, the reaction is carried out preferably at 70° C. to 80° C. The solvent for the reaction is preferably n-butanol.

Furthermore, when in Chemical Formula 1, $L_3$ is a single bond, A is represented by Chemical Formula 1', and when in Chemical Formula 1', Y is N and is a single bond, as an example, the compound represented by Chemical Formula 1 can be produced through Reaction Scheme 2 below.

[Reaction Scheme 2]

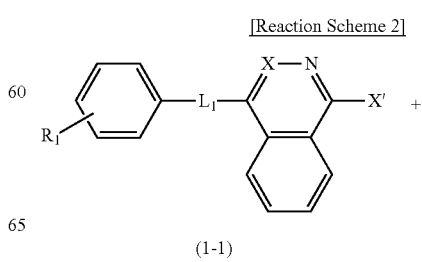

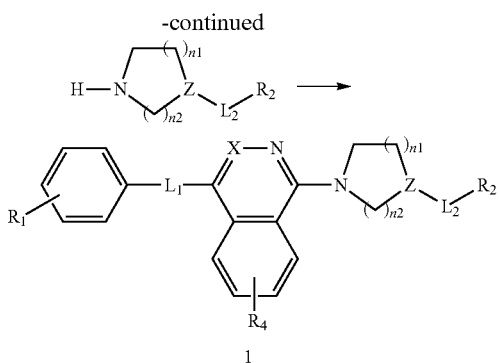

in Reaction Scheme 2, X, Z, $L_1$, $L_2$, $R_1$, $R_2$, n1 and n2 are as previously defined, and X' is halogen. More preferably, X' is chloro.

The reaction is preferably carried out in the presence of triethylamine. Also, the reaction is preferably carried out at 70° C. to 80° C. Further, the solvent for the reaction is preferably n-butanol.

Further, when in Chemical Formula 1, $L_3$ is a single bond, A is represented by Chemical Formula 1', and when in Chemical Formula 1', Y is C and is a double bond, as an example, the compound represented by Chemical Formula 1 can be produced through Reaction Scheme 3 below.

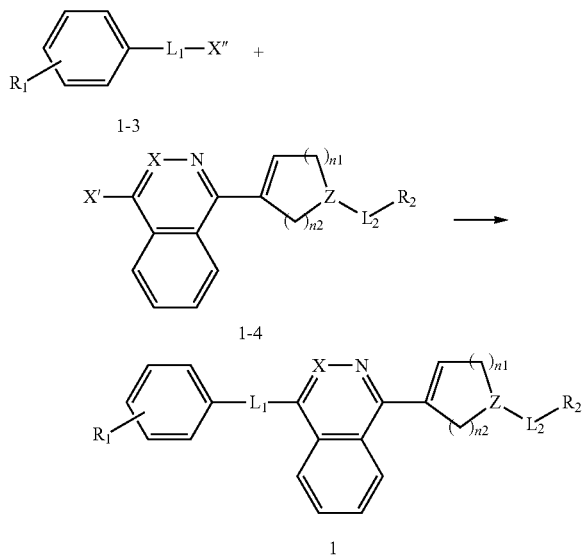

in Reaction Scheme 3, X, Z, $L_1$, $L_2$, $R_1$, $R_2$, n1 and n2 are as previously defined, X' is halogen, and X" is $B(OH)_2$. More preferably, X' is chloro.

The reaction is preferably carried out in the presence of $Pd(PPh_3)_4$ and $Na_2CO_3$. Also, the reaction is preferably carried out at 100° C. to 120° C. Further, the solvent for the reaction is preferably dioxane, dimethylformamide, water or a mixed solvent thereof.

The preparation method of the compound represented by Chemical Formula 1 according to the present invention is not limited to the above-mentioned reaction schemes 1 and 2, and modification can be made thereto as necessary. A specific preparation method of the compound represented by Chemical Formula 1 according to the present invention can be further embodied through the following Examples.

Further, the present invention provides a pharmaceutical composition for preventing or treating cardiovascular diseases, comprising the compound represented by Chemical Formula 1, or a pharmaceutically acceptable salt, hydrate, solvate or isomer thereof as an active ingredient.

The compound according to the present invention can be used for preventing or treating cardiovascular diseases by inhibiting the binding of resistin and CAP1 and thereby inhibiting the expression of inflammatory cytokines. The cardiovascular disease includes arteriosclerosis, hypertension, angina pectoris, myocardial infarction, or stroke.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like. but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, or the like through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of cardiovascular diseases.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of 2-(4-(4-phenylphthalazin-1-yl)piperazin-1-yl)ethanol

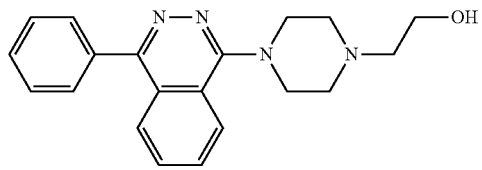 [SMILES: OCCN1CCN(c2nnc(-c3ccccc3)c3ccccc23)CC1]

1-Chloro-4-phenylphthalazine (0.1 g, 0.42 mmol) and 2-(piperazin-1-yl)ethan-1-ol (0.11 mL, 0.83 mmol) were dissolved in n-butanol (3 mL). The mixture was stirred for 3 hours while maintaining an internal temperature at 70° C. to 80° C., and the termination of the reaction was confirmed by TLC. The reaction solution was concentrated under reduced pressure, and then the resulting residue was separated by column chromatography to obtain the title compound (0.12 g, 86.5%).

1H NMR (500 MHz, MeOD): 7.93 (d, 1H), 7.62 (d, 1H), 7.27 (s, 1H), 7.21 (m, 2H), 7.07 (d, 1H), 6.69 (d, 1H), 5.05 (d, 2H), 3.76 (s, 3H), 3.11 (t, 2H), 2.81 (t, 2H), 1.96 (s, 4H)

Hereinafter, compounds of Examples 2 to 11 were each produced in the same manner as in Example 1, except that reactants corresponding to the chemical structure of the compound to be produced were used.

Example 2: Preparation of 1-(4-(4-p-tolyl phthalazin-1-yl)piperazin-1-yl)ethanone

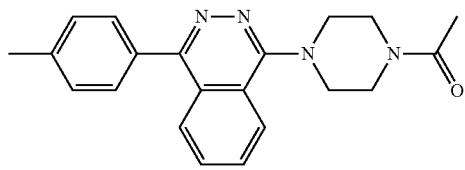

1H NMR (500 MHz, MeOD): 8.29 (d, 1H), 8.00 (t, 2H), 7.91 (t, 1H), 7.54 (d, 2H), 7.41 (d, 2H), 3.91 (t, 2H), 3.87 (t, 2H), 3.58 (t, 2H), 3.51 (t, 2H), 2.47 (s, 3H), 2.20 (s, 3H)

Example 3: Preparation of 1-(4-methyl-1,4-diazepan-1-yl)-4-phenylphthalazine

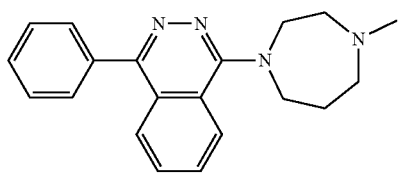 [SMILES: CN1CCCN(c2nnc(-c3ccccc3)c3ccccc23)CC1]

1H NMR (500 MHz, MeOD): 8.24 (d, 1H), 7.91 (d, 2H), 7.85 (d, 1H), 7.64 (d, 2H), 7.56 (m, 3H), 4.00 (m, 2H), 3.95 (t, 2H), 2.99 (t, 2H), 2.82 (t, 2H), 2.45 (s, 3H), 2.17 (t, 2H)

Example 4: Preparation of 2-(1-(4-(4-chlorophenyl)phthalazin-1-yl)piperidin-4-yl)ethanol

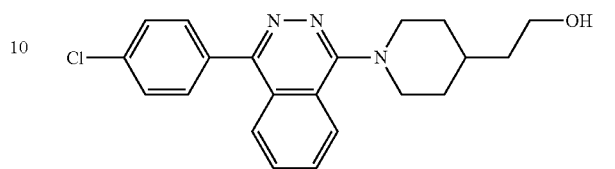

1H NMR (500 MHz, CDCl$_3$): 8.11 (d, 1H), 7.95 (d, 1H), 7.83 (t, 1H), 7.78 (t, 1H), 7.68 (d, 2H), 7.51 (d, 2H), 4.02 (d, 2H), 3.80 (t, 2H), 3.17 (t, 2H), 1.94 (d, 2H), 1.79 (m, 1H), 1.64 (m, 4H)

Example 5: Preparation of 2-(4-(4-(4-chlorophenyl)phthalazin-1-yl)piperazin-1-yl)-N,N-dimethyl-ethanamine

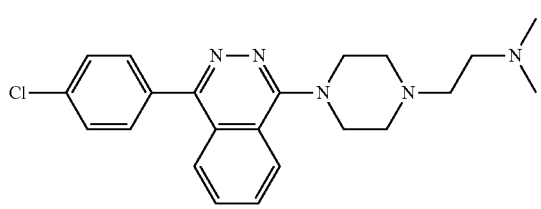 [SMILES: CN(C)CCN1CCN(c2nnc(-c3ccc(Cl)cc3)c3ccccc23)CC1]

1H NMR (500 MHz, CDCl$_3$): 8.12 (d, 1H), 7.96 (d, 1H), 7.83 (t, 1H), 7.78 (t, 1H), 7.68 (d, 2H), 7.51 (d, 2H), 3.70 (m, 4H), 2.80 (m, 4H), 2.77 (m, 4H), 2.52 (s, 6H)

Example 6: Preparation of 1-(4-chlorophenyl)-4-(4-(pyridin-2-yl)piperazin-1-yl)phthalazine

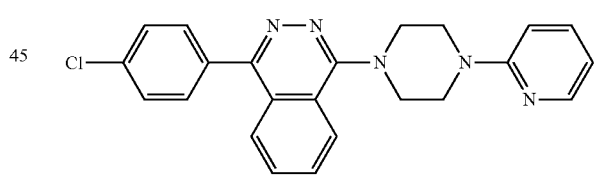

1H NMR (500 MHz, CDCl$_3$): 8.25 (d, 1H), 8.19 (d, 1H), 7.98 (d, 1H), 7.88 (t, 1H), 7.81 (t, 1H), 7.69 (d, 2H), 7.53 (m, 3H), 6.77 (d, 1H), 6.69 (t, 1H), 3.86 (br, 4H), 3.73 (br, 4H)

Example 7: Preparation of 1-(4-chlorophenyl)-4-(4-(pyrrolidin-1-yl)piperidin-1-yl)phthalazine

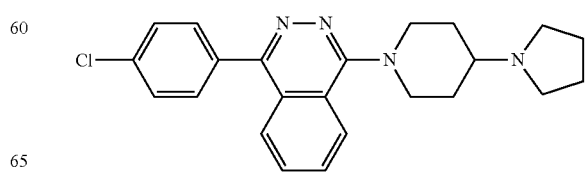

1H NMR (500 MHz, CDCl₃): 8.13 (d, 1H), 7.97 (d, 1H), 7.97 (t, 1H), 7.80 (t, 1H), 7.67 (d, 2H), 7.52 (d, 2H), 4.07 (d, 2H), 3.82 (s, 2H), 3.16 (t, 2H), 2.93 (br, 2H), 2.49 (br, 2H), 2.28 (m, 3H), 2.08 (br, 2H), 1.58 (br, 2H)

Example 8: Preparation of 4-(1-(4-(4-chlorophenyl)phthalazin-1-yl)piperidin-4-yl)morpholine

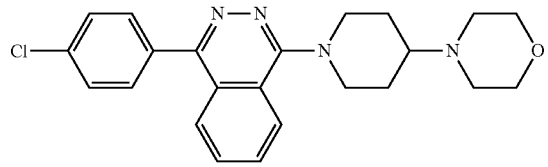 [SMILES: Clc1ccc(-c2nnc(N3CCC(N4CCOCC4)CC3)c3ccccc23)cc1]

1H NMR (500 MHz, CDCl₃): 8.09 (d, 1H), 7.95 (d, 1H), 7.83 (t, 1H), 7.77 (t, 1H), 7.68 (d, 2H), 7.51 (d, 2H), 4.06 (d, 2H), 3.78 (m, 3H), 3.15 (t, 2H), 2.66 (br, 3H), 2.50 (br, 1H), 2.09 (m, 2H), 1.88 (m, 2H), 1.60 (br, 2H)

Example 9: Preparation of 1-(4-chlorophenyl)-4-(4-(2-methoxyethyl)piperazin-1-yl)phthalazine

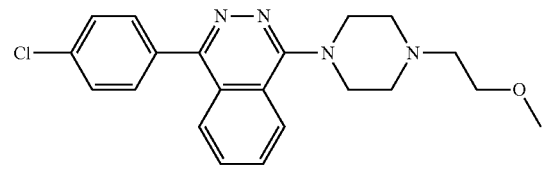 [SMILES: COCCN1CCN(c2nnc(-c3ccc(Cl)cc3)c3ccccc23)CC1]

1H NMR (500 MHz, MeOD): 8.23 (d, 1H), 7.98 (t, 1H), 7.92 (m, 2H), 7.65 (d, 2H), 7.60 (d, 2H), 3.61 (m, 6H), 3.38 (s, 3H), 2.87 (m, 4H), 2.74 (t, 2H)

Example 10: Preparation of (4-(4-(4-chlorophenyl)phthalazin-1-yl)piperazin-1-yl)(cyclopropyl)methanone

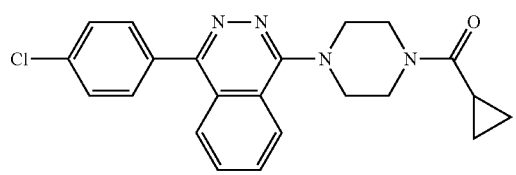 [SMILES: O=C(C1CC1)N1CCN(c2nnc(-c3ccc(Cl)cc3)c3ccccc23)CC1]

1H NMR (500 MHz, CDCl₃): 8.14 (d, 1H), 7.99 (d, 1H), 7.88 (t, 1H), 7.81 (t, 1H), 7.69 (d, 2H), 7.53 (d, 2H), 4.00 (m, 4H), 3.70 (br, 2H), 3.55 (br, 2H), 1.83 (m, 1H), 1.06 (m, 2H), 0.83 (m, 2H)

Example 11: Preparation of 2-(1-(6-(4-chlorophenyl)pyridazin-3-yl)piperidin-4-yl)ethanol

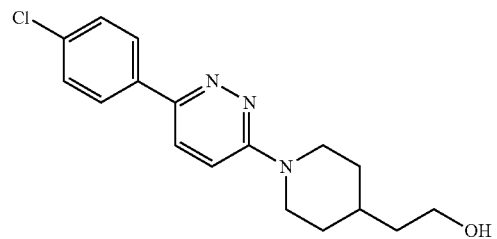 [SMILES: OCCC1CCN(c2ccc(-c3ccc(Cl)cc3)nn2)CC1]

1H NMR (500 MHz, MeOD): 7.91 (d, 2H), 7.81 (d, 1H), 7.47 (d, 2H), 7.31 (d, 1H), 4.43 (d, 2H), 3.65 (t, 2H), 3.00 (t, 2H), 1.85 (d, 2H), 1.80 (m, 1H), 1.52 (m, 2H), 1.27 (m, 2H)

Example 12: Preparation of cyclopropyl(4-(4-(4-fluorophenyl)phthalazin-1-yl)piperazin-1-yl)methanone

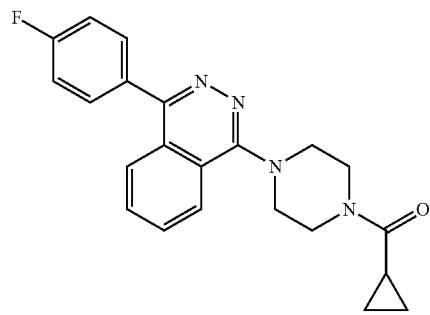

Step 1) Preparation of (4-(4-chlorophthalazin-1-yl)piperazin-1-yl)(cyclopropyl)methanone 1,4-Dichlorophthalazine (1.0 g, 5.03 mmol) and piperazine (0.70 g, 10.06 mmol) were dissolved in n-butanol (10 mL). The mixture was stirred for 3 hours while maintaining an internal temperature at 70° C. to 80° C., and the termination of the reaction was confirmed by TLC. The reaction solution was concentrated under reduced pressure, and then the obtained residue was dissolved in dichloromethane (10 mL) and then cooled to 0° C. Thereafter, cyclopropanecarbonyl chloride (0.55 mL, 6.04 mmol) and triethylamine (0.84 mL, 6.04 mmol) were added thereto, followed by stirring for 1 hour. After the termination of the reaction was confirmed by TLC, the reaction solution was washed with water and then concentrated under reduced pressure. The resulting residue was purified by column chromatography. Thereby, the desired intermediate (1.3 g, 81.7%) was obtained.

Step 2) Preparation of cyclopropyl(4-(4-(4-fluorophenyl)phthalazin-1-yl)piperazin-1-yl)methanone (4-(4-chlorophthalazin-1-yl)piperazin-1-yl)(cyclopropyl)methanone (0.05 g, 0.16 mmol) prepared in the above, Pd(PPh₃)₄ (0.01 g, 0.02 mmol) and (4-fluorophenyl) boronic acid (0.02 g, 0.24 mmol) were dissolved in dioxane (2 mL)

and 2N Na$_2$CO$_3$ aqueous solution (1 mL). The reaction solution was reacted using a microwave organic synthesis at 120° C. for 30 minutes. After the termination of the reaction was confirmed by TLC, water (5 mL) was added to the reaction and extracted twice with ethyl acetate (5 mL). The organic layer was dried over MgSO$_4$ and then concentrated under reduced pressure. The resulting residue was separated and purified by chromatography to obtain the desired title compound (0.02 g, 36.8%).

1H NMR (500 MHz, MeOD): 8.32 (d, 1H), 8.00 (dd, 1H), 7.95 (m, 2H), 7.70 (dd, 2H), 7.34 (t, 2H), 4.10 (br, 2H), 3.92 (br, 2H), 3.63 (br, 2H), 3.53 (br, 2H), 2.05 (m, 1H), 0.93 (m, 2H), 0.87 (m, 2H)

Hereinafter, compounds of Examples 13 to 30 were each produced in the same manner as in Example 12, except that reactants corresponding to the chemical structure of the compound to be produced were used.

Example 13: Preparation of cyclopropyl(4-(4-(2-fluorophenyl)phthalazin-1-yl)piperazin-1-yl)methanone

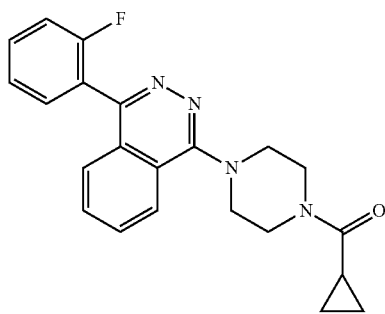 [SMILES: O=C(C1CC1)N1CCN(c2nnc(-c3ccccc3F)c3ccccc23)CC1]

1H NMR (500 MHz, MeOD): 8.33 (d, 1H), 8.01 (t, 1H), 7.93 (t, 1H), 7.71 (d, 1H), 7.63 (m, 1H), 7.58 (m, 1H), 7.41 (t, 1H), 7.35 (t, 1H), 4.11 (br, 2H), 3.93 (br, 2H), 3.66 (br, 2H), 3.57 (br, 2H), 2.05 (m, 1H), 0.94 (m, 2H), 0.86 (m, 2H)

Example 14: Preparation of cyclopropyl(4-(4-(3-fluorophenyl)phthalazin-1-yl)piperazin-1-yl)methanone

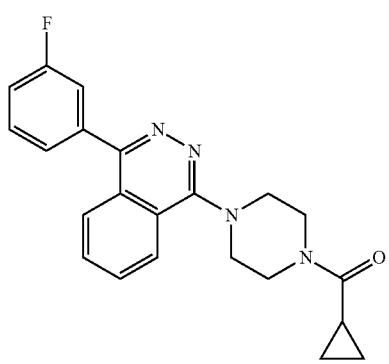 [SMILES: O=C(C1CC1)N1CCN(c2nnc(-c3cccc(F)c3)c3ccccc23)CC1]

1H NMR (500 MHz, MeOD): 8.34 (d, 1H), 8.03 (t, 1H), 7.96 (m, 2H), 7.62 (dd, 1H), 7.49 (d, 1H), 7.43 (d, 1H), 7.35 (t, 1H), 4.10 (br, 2H), 3.93 (br, 2H), 3.66 (br, 2H), 3.56 (br, 2H), 2.06 (m, 1H), 0.93 (m, 2H), 0.87 (m, 2H)

Example 15: Preparation of (4-(4-(3-chlorophenyl)phthalazin-1-yl)piperazin-1-yl)(cyclopropyl)methanone

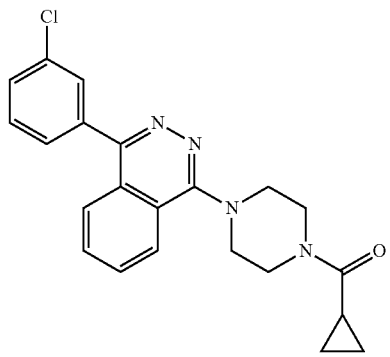 [SMILES: O=C(C1CC1)N1CCN(c2nnc(-c3cccc(Cl)c3)c3ccccc23)CC1]

1H NMR (500 MHz, MeOD): 8.32 (d, 1H), 8.02 (t, 1H), 7.95 (d, 2H), 7.70 (s, 1H), 7.60 (s, 3H), 4.11 (br, 2H), 3.93 (br, 2H), 3.65 (br, 2H), 3.55 (br, 2H), 2.07 (m, 1H), 0.94 (m, 2H), 0.87 (m, 2H)

Example 16: Preparation of cyclopropyl(4-(4-(4-methoxyphenyl)phthalazin-1-yl)piperazin-1-yl)methanone

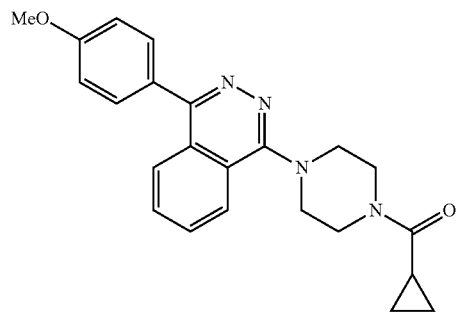 [SMILES: COc1ccc(-c2nnc(N3CCN(C(=O)C4CC4)CC3)c3ccccc23)cc1]

1H NMR (500 MHz, MeOD): 8.32 (d, 1H), 8.04 (d, 1H), 8.03 (t, 1H), 7.99 (t, 1H), 7.60 (d, 2H), 7.14 (d, 2H), 4.10 (br, 2H), 3.90 (br, 2H), 3.61 (br, 2H), 3.51 (br, 2H), 2.05 (m, 1H), 0.94 (m, 2H), 0.87 (m, 2H)

Example 17: Preparation of 4-(4-(4-(cyclopropanecarbonyl)piperazin-1-yl)phthalazin-1-yl)benzonitrile

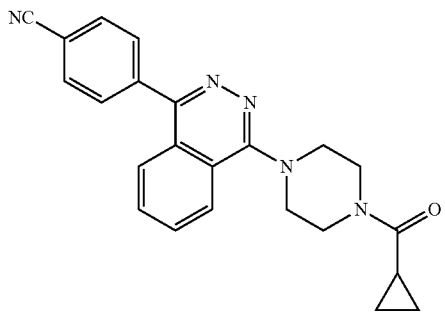 [SMILES: N#Cc1ccc(-c2nnc(N3CCN(C(=O)C4CC4)CC3)c3ccccc23)cc1]

1H NMR (500 MHz, MeOD): 8.35 (d, 1H), 8.03 (t, 1H), 7.96 (m, 4H), 7.87 (d, 2H), 4.11 (br, 2H), 3.93 (br, 2H), 3.66 (br, 2H), 3.56 (br, 2H), 2.06 (m, 1H), 0.94 (m, 2H), 0.87 (m, 2H)

Example 18: Preparation of cyclopropyl(4-(4-(4-nitrophenyl)phthalazin-1-yl)piperazin-1-yl)methanone

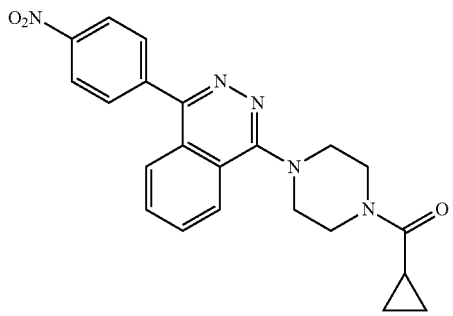 [SMILES: O=C(C1CC1)N1CCN(c2nnc(-c3ccc([N+](=O)[O-])cc3)c3ccccc23)CC1]

1H NMR (500 MHz, MeOD): 8.75 (d, 2H), 8.34 (d, 1H), 8.04 (t, 1H), 7.96 (m, 4H), 4.11 (br, 2H), 3.93 (br, 2H), 3.66 (br, 2H), 3.58 (br, 2H), 2.07 (m, 1H), 0.94 (m, 2H), 0.87 (m, 2H)

Example 19: Preparation of cyclopropyl(4-(4-(2-fluoro-4-methoxyphenyl)phthalazin-1-yl)piperazin-1-yl)methanone

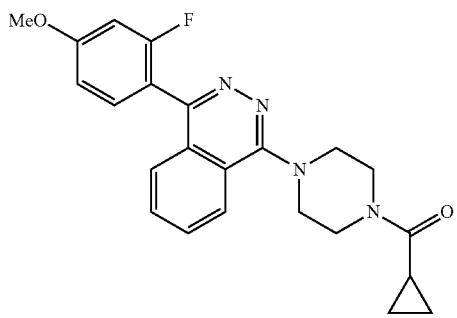 [SMILES: COc1ccc(-c2nnc(N3CCN(C(=O)C4CC4)CC3)c3ccccc23)c(F)c1]

1H NMR (500 MHz, MeOD): 8.27 (d, 1H), 7.97 (t, 1H), 7.89 (t, 1H), 7.74 (d, 1H), 7.47 (t, 1H), 6.97 (d, 1H), 6.90 (d, 1H), 4.08 (br, 2H), 3.90 (m, 5H), 3.62 (br, 2H), 3.52 (br, 2H), 2.03 (m, 1H), 0.93 (m, 2H), 0.85 (m, 2H)

Example 20: Preparation of cyclopropyl(4-(4-phenylisoquinolin-1-yl)piperazin-1-yl)methanone

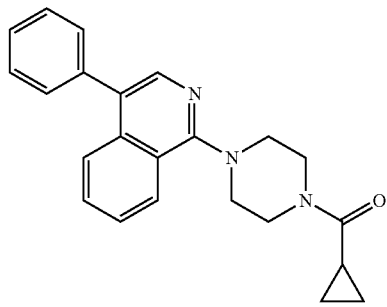 [SMILES: O=C(C1CC1)N1CCN(c2ncc(-c3ccccc3)c3ccccc23)CC1]

1H NMR (500 MHz, MeOD): 8.27 (d, 1H), 7.98 (s, 1H), 7.80 (d, 1H), 7.62 (m, 2H), 7.48 (m, 2H), 7.42 (m, 3H), 4.03 (br, 2H), 3.87 (br, 2H), 3.44 (br, 2H), 3.34 (br, 2H), 2.03 (m, 1H), 0.92 (m, 2H), 0.85 (m, 2H)

Example 21: Preparation of cyclopropyl(4-(4-(4-fluorophenyl)isoquinolin-1-yl)piperazin-1-yl)methanone

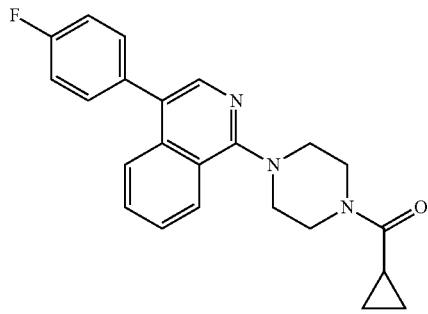 [SMILES: O=C(C1CC1)N1CCN(c2ncc(-c3ccc(F)cc3)c3ccccc23)CC1]

1H NMR (500 MHz, MeOD): 8.27 (d, 1H), 7.96 (s, 1H), 7.74 (d, 1H), 7.62 (m, 2H), 7.41 (m, 2H), 7.21 (m, 2H), 4.02 (br, 2H), 3.86 (br, 2H), 3.42 (br, 2H), 3.33 (br, 2H), 1.99 (m, 1H), 0.92 (m, 2H), 0.84 (m, 2H)

Example 22: Preparation of (4-(4-(4-chlorophenyl)isoquinolin-1-yl)piperazin-1-yl)(cyclopropyl)methanone

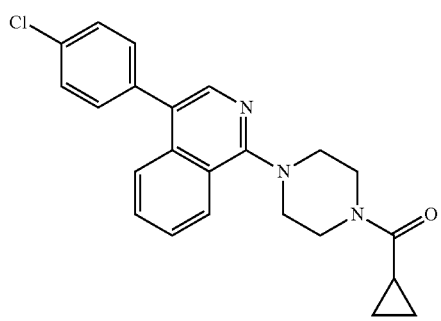 [SMILES: O=C(C1CC1)N1CCN(c2ncc(-c3ccc(Cl)cc3)c3ccccc23)CC1]

1H NMR (500 MHz, MeOD): 8.27 (d, 1H), 7.97 (s, 1H), 7.75 (d, 1H), 7.63 (m, 2H), 7.47 (d, 2H), 7.39 (d, 2H), 4.03

(br, 2H), 3.86 (br, 2H), 3.44 (br, 2H), 3.25 (br, 2H), 2.00 (m, 1H), 0.92 (m, 2H), 0.85 (m, 2H)

Example 23: Preparation of cyclopropyl(4-(4-(4-methoxyphenyl)isoquinolin-1-yl)piperazin-1-yl)methanone

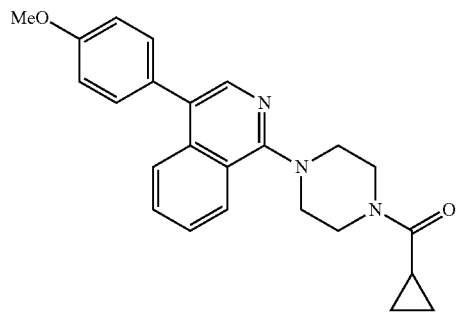 [SMILES: COc1ccc(-c2cnc(N3CCN(C(=O)C4CC4)CC3)c3ccccc23)cc1]

1H NMR (500 MHz, MeOD): 8.23 (d, 1H), 7.94 (s, 1H), 8.80 (d, 1H), 7.59 (m, 2H), 7.30 (d, 2H), 7.01 (d, 2H), 4.00 (br, 2H), 3.83 (br, 2H), 3.40 (br, 2H), 3.31 (br, 2H), 2.00 (m, 1H), 0.92 (m, 2H), 0.84 (m, 2H)

Example 24: Preparation of (E)-(4-(4-(4-chlorostyryl)phthalazin-1-yl)piperazin-1-yl)(cyclopropyl)methanone

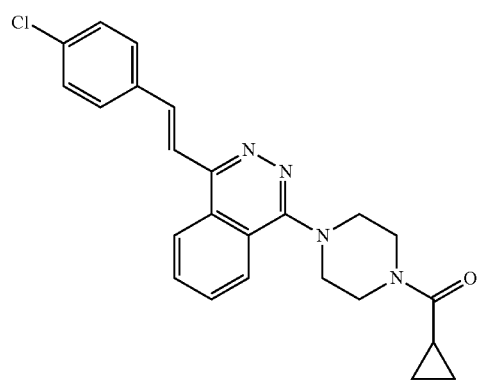 [SMILES: O=C(C1CC1)N1CCN(c2nnc(/C=C/c3ccc(Cl)cc3)c3ccccc23)CC1]

1H NMR (500 MHz, MeOD): 8.47 (d, 1H), 8.27 (d, 1H), 8.00 (m, 3H), 7.76 (m, 3H), 7.46 (d, 2H), 4.10 (br, 2H), 3.91 (br, 2H), 3.60 (br, 2H), 3.50 (br, 2H), 2.06 (m, 1H), 0.93 (m, 2H), 0.88 (m, 2H)

Example 25: Preparation of (E)-(4-(4-(4-chlorostyryl)isoquinolin-1-yl)piperazin-1-yl)(cyclopropyl)methanone

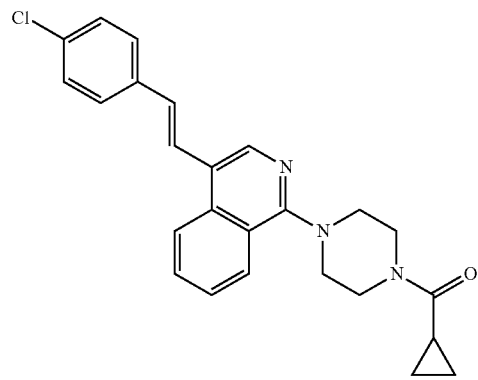 [SMILES: O=C(C1CC1)N1CCN(c2ncc(/C=C/c3ccc(Cl)cc3)c3ccccc23)CC1]

1H NMR (500 MHz, MeOD): 8.33 (s, 1H), 8.26 (d, 1H), 8.22 (d, 1H), 7.77 (m, 2H), 7.66 (d, 1H), 7.62 (d, 2H), 7.36 (d, 2H), 7.12 (d, 1H), 4.05 (br, 2H), 3.88 (br, 2H), 3.45 (br, 2H), 3.36 (br, 2H), 2.03 (m, 1H), 0.93 (m, 2H), 0.86 (m, 2H)

Example 26: Preparation of (E)-cyclopropyl(4-(4-styrylisoquinolin-1-yl)piperazin-1-yl)methanone

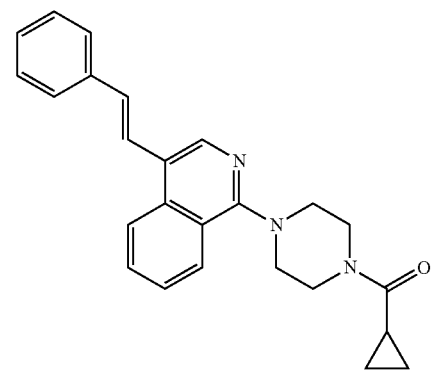 [SMILES: O=C(C1CC1)N1CCN(c2ncc(/C=C/c3ccccc3)c3ccccc23)CC1]

1H NMR (500 MHz, MeOD): 8.34 (s, 1H), 8.25 (d, 1H), 8.22 (d, 1H), 7.78 (d, 1H), 7.76 (d, 1H), 7.65 (m, 3H), 7.38 (m, 2H), 7.28 (t, 1H), 7.15 (d, 1H), 4.05 (br, 2H), 3.88 (br, 2H), 3.45 (br, 2H), 3.36 (br, 2H), 2.04 (m, 1H), 0.93 (m, 2H), 0.86 (m, 2H)

Example 27: Preparation of (E)-cyclopropyl(4-(4-(3-phenylprop-1-enyl)phthalazin-1-yl)piperazin-1-yl)methanone

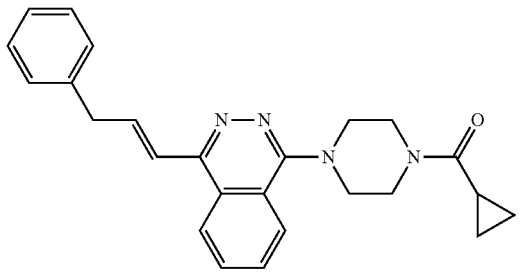 [SMILES: O=C(C1CC1)N1CCN(c2nnc(/C=C/Cc3ccccc3)c3ccccc23)CC1]

1H NMR (500 MHz, MeOD): 8.32 (td, 1H), 8.27 (td, 1H), 7.97 (m, 2H), 7.33 (d, 2H), 7.25 (t, 2H), 7.17 (t, 1H), 6.56 (m, 2H), 4.19 (d, 2H), 4.08 (br, 2H), 3.90 (br, 2H), 3.55 (br, 2H), 3.45 (br, 2H), 2.05 (m, 1H), 0.93 (m, 2H), 0.86 (m, 2H)

Example 28: Preparation of (E)-cyclopropyl(4-(4-(3-phenylprop-1-enyl)isoquinolin-1-yl)piperazin-1-yl)methanone

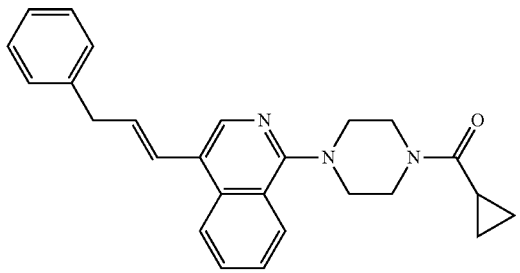 [SMILES: O=C(C1CC1)N1CCN(c2ncc(/C=C/Cc3ccccc3)c3ccccc23)CC1]

1H NMR (500 MHz, MeOD): 8.21 (d, 1H), 8.11 (s, 1H), 8.03 (d, 1H), 7.72 (t, 1H), 7.61 (t, 1H), 7.30 (m, 3H), 7.21 (m, 1H), 6.95 (d, 1H), 6.34 (td, 1H), 4.01 (br, 2H), 3.85 (br, 2H), 3.63 (d, 2H), 3.38 (br, 2H), 3.30 (br, 2H), 2.01 (m, 1H), 0.91 (m, 2H), 0.84 (m, 2H)

Example 29: Preparation of (4-(4-(4-chlorophenyl)phthalazin-1-yl)-1,4-diazepan-1-yl)(cyclopropyl)methanone

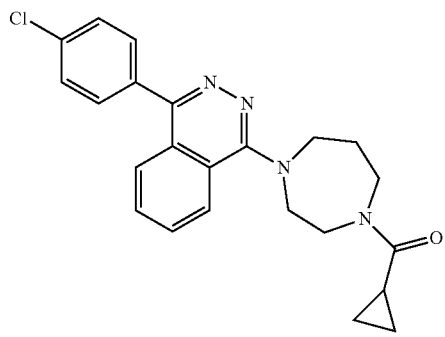 [SMILES: O=C(C1CC1)N1CCCN(c2nnc(-c3ccc(Cl)cc3)c3ccccc23)CC1]

1H NMR (500 MHz, MeOD): 8.13 (d, 1H), 7.97 (t, 1H), 7.83 (m, 2H), 7.70 (d, 2H), 7.52 (d, 2H), 4.07 (d, 2H), 3.92-3.60 (m, 6H), 2.11 (m, 2H), 1.81 (m, 1H), 1.00 (m, 2H), 0.79 (m, 2H)

Example 30: Preparation of 1-(4-chlorophenyl)-4-(4-(2-methoxyethyl)-1,4-diazepan-1-yl)phthalazine

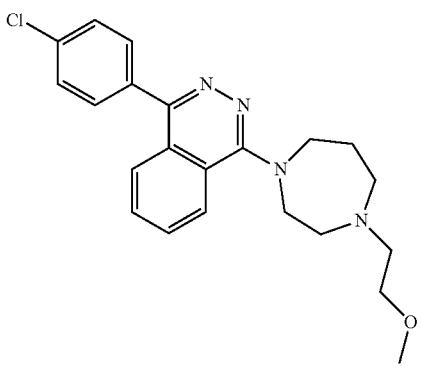 [SMILES: COCCN1CCCN(c2nnc(-c3ccc(Cl)cc3)c3ccccc23)CC1]

1H NMR (500 MHz, MeOD): 8.26 (d, 1H), 7.80 (m, 3H), 7.65 (d, 2H), 7.60 (d, 2H), 4.06 (m, 2H), 3.96 (t, 2H), 3.66 (m, 5H), 3.39 (m, 4H), 3.20 (m, 2H), 2.25 (m, 2H)

Example 31: Preparation of 2-amino-1-(4-(4-(4-chlorophenyl)phthalazin-1-yl)piperazin-1-yl)ethanone hydrochloride

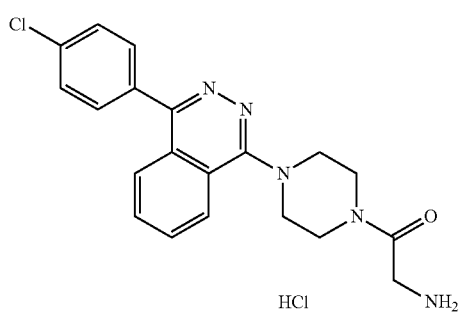 [SMILES: NCC(=O)N1CCN(c2nnc(-c3ccc(Cl)cc3)c3ccccc23)CC1 ; Cl]

Step 1) Preparation of 1-(4-chlorophenyl)-4-(piperazin-1-yl)phthalazine

Tert-butylpiperazine-1-carboxylate was used instead of piperazine in step 1 of Example 12, and subsequent additional acylation was not carried out, (4-chlorophenyl)boronic acid was used instead of (4-fluorophenyl)boronic acid in Step 2 to prepare an intermediate.

The obtained intermediate tert-butyl 4-(4-(4-chlorophenyl)phthalazin-1-yl)piperazine-1-carboxylate (1.0 g, 2.35 mmol) was dissolved in dichloromethane (8 mL), and then acetic acid (2 mL) was added thereto. The reaction solution was stirred at room temperature for 4 hours, and the termination of the reaction was confirmed by TLC. The reaction mixture was washed with a saturated aqueous solution of NaHCO$_3$, and then concentrated under reduced pressure.

The resulting residue was separated and purified by column chromatography to obtain the title compound (0.55 g, 71.9%).

Step 2) Preparation of tert-butyl (2-(4-(4-(4-chlorophenyl)phthalazin-1-yl)piperazin-1-yl)-2-oxoethyl) carbamate The obtained intermediate 1-(4-chlorophenyl)-4-(piperazin-1-yl)phthalazine (0.03 g, 0.92 mmol), N-Boc-Gly (0.02 g, 1.35 mmol), EDC-HCl (0.03 g, 1.35 mmol) and HOBt (0.02 g, 1.35 mmol) were dissolved in dichloromethane (1 mL), and then DIPEA (0.02 uL, 1.84 mmol) was added thereto. The reaction mixture was stirred overnight at room temperature, and the termination of the reaction was confirmed by TLC. Water (2 mL) was added to the reaction mixture, and the mixture was washed twice with dichloromethane (2 mL). The resulting residue was separated and purified by chromatography (PLC) to obtain the desired intermediate (0.02 g, 60.3%).

Step 3) Preparation of 2-amino-1-(4-(4-(4-chlorophenyl) phthalazin-1-yl)piperazin-1-yl)ethanone hydrochloride The obtained intermediate tert-butyl (2-(4-(4-(4-chlorophenyl)phthalazin-1-yl)piperazin-1-yl)-2-oxoethyl)carbamate (0.02 g, 0.04 mmol) was dissolved in 1N HCl ethyl acetate solution (1 mL), and then the mixture was stirred overnight at 50° C. to 60° C. After confirming that a solid not soluble in the organic solvent was produced, the reaction solution was filtered. The obtained compound was dried under reduced pressure to obtain the desired compound (0.01 g, 57.5%).

1H NMR (500 MHz, MeOD): 8.53 (m, 1H), 8.30 (m, 1H), 8.21 (m, 2H), 7.77 (m, 4H), 4.07 (br, 2H), 3.99 (br, 2H), 3.87 (br, 2H), 3.83 (br, 4H)

Example 32: Preparation of 1-(4-chlorophenyl)-4-(4-(methylsulfonyl)piperazin-1-yl)phthalazine

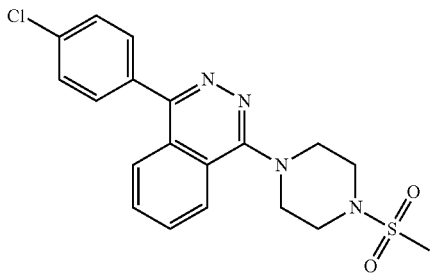 [SMILES: CS(=O)(=O)N1CCN(c2nnc(-c3ccc(Cl)cc3)c3ccccc23)CC1]

Intermediate 1-(4-chlorophenyl)-4-(piperazin-1-yl)phthalazine (0.03 g, 0.92 mmol) obtained in the step 1 of Example 31 and triethylamine (0.02 mL, 0.14 mmol) were dissolved in dichloromethane (2 mL), and then methane sulfonyl chloride (0.01 mL, 0.11 mmol) was added thereto. The reaction mixture was stirred for 3 hours, and the termination of the reaction was confirmed by TLC. Water (2 mL) was added to the reaction mixture and the mixture was washed twice with dichloromethane (2 mL), and the resulting residue was crystallized using ethyl acetate and n-hexane. The obtained solid was filtered to obtain the desired compound (0.02 g, 36.8%).

1H NMR (500 MHz, MeOD): 8.09 (d, 1H), 8.00 (d, 1H), 7.88 (t, 1H), 7.82 (t, 1H), 7.68 (d, 2H), 7.53 (d, 2H), 3.77 (t, 4H), 3.54 (t, 4H), 2.86 (s, 3H)

Hereinafter, compounds of Examples 33 and 34 were each produced in the same manner as in Example 32, except that reactants corresponding to the chemical structure of the compound to be produced were used.

Example 33: Preparation of 1-(4-chlorophenyl)-4-(4-(tetrahydro-2H-pyran-4-ylsulfonyl)piperazin-1-yl) phthalazine

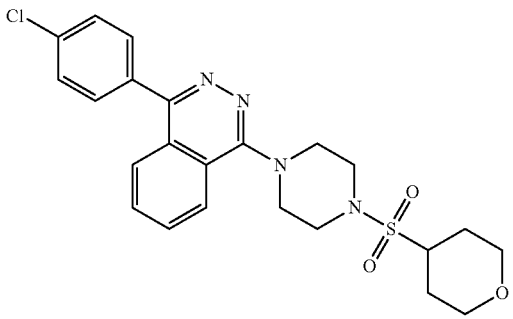 [SMILES: O=S(=O)(C1CCOCC1)N1CCN(c2nnc(-c3ccc(Cl)cc3)c3ccccc23)CC1]

1H NMR (500 MHz, MeOD): 8.13 (d, 1H), 8.04 (d, 1H), 7.95 (t, 1H), 7.89 (t, 1H), 7.70 (d, 2H), 7.56 (d, 2H), 4.10 (dd, 2H), 3.77 (br, 4H), 3.69 (br, 4H), 3.40 (t, 2H), 3.22 (t, 1H), 2.01 (m, 2H), 1.93 (m, 2H)

Example 34: Preparation of 1-(4-chlorophenyl)-4-(4-(cyclopentylsulfonyl)piperazin-1-yl)phthalazine

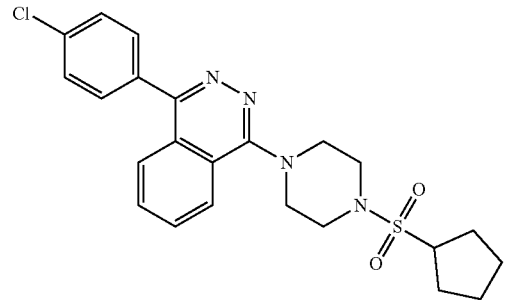 [SMILES: O=S(=O)(C1CCCC1)N1CCN(c2nnc(-c3ccc(Cl)cc3)c3ccccc23)CC1]

1H NMR (500 MHz, MeOD): 8.09 (d, 1H), 7.99 (d, 1H), 7.88 (t, 1H), 7.81 (t, 1H), 7.67 (d, 2H), 7.53 (d, 2H), 3.69 (br, 4H), 3.63 (br, 4H), 3.51 (m, 1H), 2.04 (m, 4H), 1.82 (m, 2H), 1.63 (m, 2H)

Hereinafter, compounds of Examples 35 and 36 were each produced in the same manner as in Example 31, except that reactants corresponding to the chemical structure of the compound to be produced were used.

Example 35: Preparation of (1-aminocyclobutyl)(4-(4-(4-chlorophenyl)phthalazin-1-yl)piperazin-1-yl)methanone hydrochloride

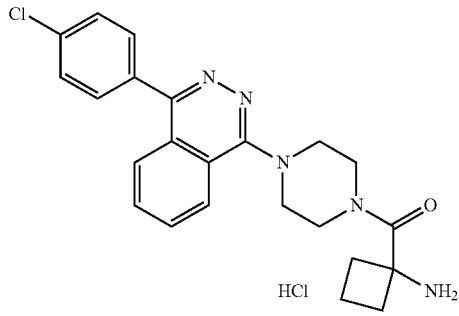 [SMILES: NC1(C(=O)N2CCN(c3nnc(-c4ccc(Cl)cc4)c4ccccc34)CC2)CCC1 ; Cl]

1H NMR (500 MHz, MeOD): 8.54 (m, 1H), 8.35 (m, 1H), 8.24 (m, 2H), 7.79 (m, 4H), 3.98 (br, 4H), 3.60 (br, 4H), 2.68 (m, 2H), 2.41 (m, 2H), 2.27 (m, 1H), 2.14 (m, 1H)

Example 36: Preparation of (R)-2-amino-1-(4-(4-(4-chlorophenyl)phthalazin-1-yl)piperazin-1-yl)propan-1-one hydrochloride

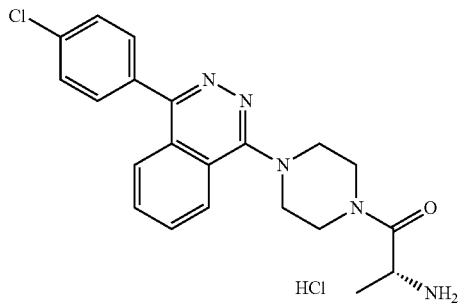 [SMILES: C[C@@H](N)C(=O)N1CCN(c2nnc(-c3ccc(Cl)cc3)c3ccccc23)CC1 ; Cl]

1H NMR (500 MHz, MeOD): 8.56 (m, 1H), 8.31 (m, 1H), 8.23 (m, 2H), 7.78 (m, 4H), 4.53 (m, 1H), 4.05 (m, 1H), 3.92 (m, 7H), 1.54 (d, 3H)

Hereinafter, a compound of Example 37 was produced in the same manner as in Example 32, except that reactants corresponding to the chemical structure of the compound to be produced were used.

Example 37: Preparation of 1-(4-chlorophenyl)-4-(4-(cyclopropylsulfonyl)piperazin-1-yl)phthalazine

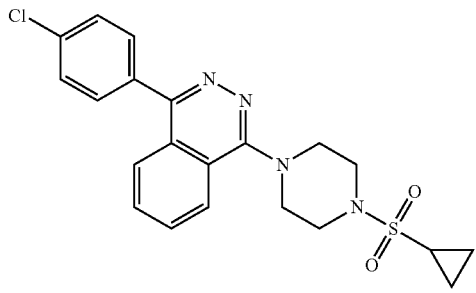 [SMILES: O=S(=O)(C1CC1)N1CCN(c2nnc(-c3ccc(Cl)cc3)c3ccccc23)CC1]

1H NMR (500 MHz, MeOD): 8.28 (d, 1H), 8.01 (t, 1H), 7.95 (m, 2H), 7.67 (d, 2H), 7.61 (d, 2H), 2.60 (m, 1H), 1.09 (m, 2H), 0.90 (m, 2H)

Hereinafter, a compound of Example 38 was produced in the same manner as in Example 12, except that reactants corresponding to the chemical structure of the compound to be produced were used. At this time, when an amine group was present in the compound to be produced, a protective group (Boc) was introduced and finally an elimination reaction of the protective group was carried out as in the step 3 of Example 31.

Example 38: Preparation of 2-(4-(4-(4-chlorophenyl)phthalazin-1-yl)piperazin-1-yl)ethanamine hydrochloride

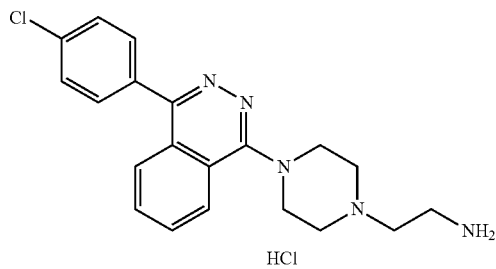 [SMILES: NCCN1CCN(c2nnc(-c3ccc(Cl)cc3)c3ccccc23)CC1 ; Cl]

1H NMR (500 MHz, MeOD): 8.30 (d, 1H), 7.99 (t, 1H), 7.94 (m, 2H), 7.68 (d, 2H), 7.37 (d, 2H), 3.88 (d, 2H), 3.65 (t, 2H), 3.26 (d, 2H), 2.46 (t, 2H), 1.92 (d, 2H)

Hereinafter, compounds of Examples 39 to 42 were each produced in the same manner as in Example 32, except that reactants corresponding to the chemical structure of the compound to be produced were used.

Example 39: Preparation of 1-(4-chlorophenyl)-4-(4-methoxypiperidin-1-yl)phthalazine

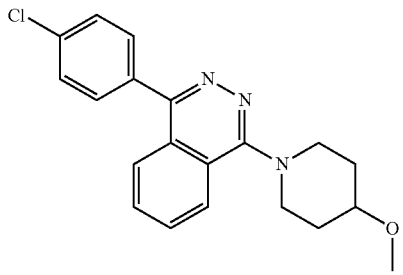 [SMILES: COC1CCN(c2nnc(-c3ccc(Cl)cc3)c3ccccc23)CC1]

1H NMR (500 MHz, CDCl$_3$): 8.10 (d, 1H), 7.95 (d, 1H), 7.84 (t, 1H), 7.77 (t, 1H), 7.68 (d, 2H), 7.51 (d, 2H), 4.80 (d, 2H), 3.87 (d, 2H), 3.52 (m, 1H), 3.44 (s, 3H), 3.31 (t, 2H), 2.18 (d, 2H), 1.88 (m, 2H)

Example 40: Preparation of 1-(4-chlorophenyl)-4-(4-ethoxypiperidin-1-yl)phthalazine

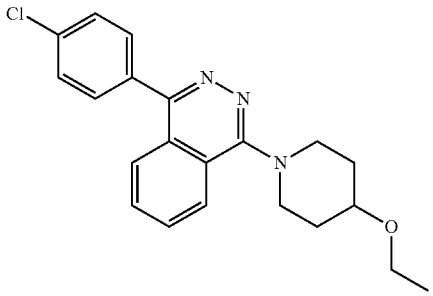 [SMILES: CCOC1CCN(c2nnc(-c3ccc(Cl)cc3)c3ccccc23)CC1]

1H NMR (500 MHz, CDCl$_3$): 8.09 (d, 1H), 7.94 (d, 1H), 7.82 (t, 1H), 7.76 (t, 1H), 7.68 (d, 2H), 7.51 (d, 2H), 3.89 (d, 2H), 3.60 (m, 2H), 3.31 (m, 3H), 2.20 (m, 2H), 1.90 (m, 2H), 1.34 (t, 3H)

Example 41: Preparation of 1-(4-chlorophenyl)-4-(4-(cyclopropylmethoxy)piperidin-1-yl)phthalazine

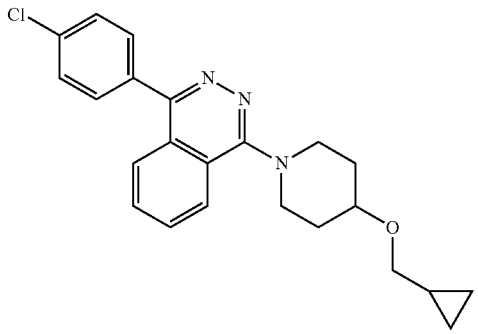 [SMILES: Clc1ccc(-c2nnc(N3CCC(OCC4CC4)CC3)c3ccccc23)cc1]

1H NMR (500 MHz, CDCl$_3$): 8.09 (d, 1H), 7.94 (d, 1H), 7.83 (t, 1H), 7.77 (t, 1H), 7.67 (d, 2H), 7.51 (d, 2H), 3.88 (d, 2H), 3.62 (m, 1H), 3.38 (d, 2H), 3.28 (t, 2H), 2.17 (d, 2H), 1.91 (dd, 2H), 0.57 (d, 2H), 0.24 (d, 2H)

Example 42: Preparation of 1-(4-(4-chlorophenyl)phthalazin-1-yl)piperidin-4-yl cyclopropanecarboxylate

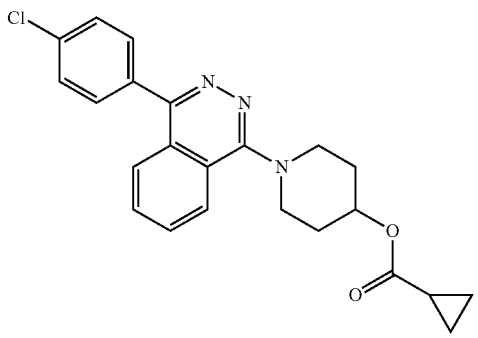 [SMILES: O=C(OC1CCN(c2nnc(-c3ccc(Cl)cc3)c3ccccc23)CC1)C1CC1]

1H NMR (500 MHz, CDCl$_3$): 8.10 (d, 1H), 7.96 (d, 1H), 7.84 (t, 1H), 7.78 (t, 1H), 7.67 (d, 2H), 7.53 (d, 2H), 5.10 (m, 1H), 3.81 (m, 2H), 3.48 (m, 2H), 2.16 (m, 2H), 2.01 (m, 3H), 1.65 (m, 1H), 1.03 (m, 2H), 0.88 (m, 2H)

Hereinafter, compounds of Examples 43 and 44 were each produced in the same manner as in Example 31, except that reactants corresponding to the chemical structure of the compound to be produced were used.

Example 43: Preparation of 2-amino-1-(4-(4-(4-chlorophenyl)phthalazin-1-yl)piperazin-1-yl)-2-methyl propan-1-one hydrochloride

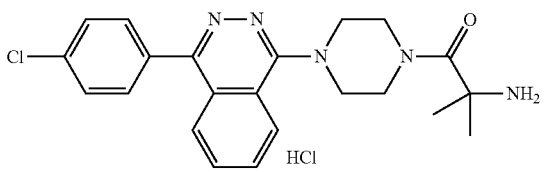 [SMILES: CC(C)(N)C(=O)N1CCN(c2nnc(-c3ccc(Cl)cc3)c3ccccc23)CC1 ; Cl]

1H NMR (500 MHz, MeOD): 8.47 (d, 1H), 8.21 (d, 1H), 8.13 (m, 2H), 7.72 (d, 4H), 4.03 (br, 4H), 3.78 (br, 4H), 1.75 (s, 6H)

Example 44: Preparation of 2-amino-1-(4-(4-(4-chlorophenyl)phthalazin-1-yl)-5,6-dihydropyridin-1(2H)-yl)-2-methylpropan-1-one hydrochloride

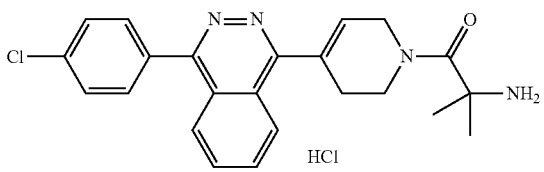 [SMILES: CC(C)(N)C(=O)N1CC=C(c2nnc(-c3ccc(Cl)cc3)c3ccccc23)CC1 ; Cl]

1H NMR (500 MHz, MeOD): 8.45 (d, 1H), 8.23 (d, 1H), 7.83 (t, 2H), 7.79 (d, 2H), 7.72 (d, 2H), 6.40 (s, 1H), 4.03 (br, 4H), 3.78 (br, 3H), 1.60 (s, 6H)

Hereinafter, compounds of Examples 45 and 46 were each produced in the same manner as in Example 12, except that reactants corresponding to the chemical structure of the compound to be produced were used. At this time, when an amine group was present in the compound to be produced, a protective group (Boc) was introduced and finally an elimination reaction of the protective group was carried out as in Step 3 of Example 31.

Example 45: Preparation of N-(1-(4-(4-chlorophenyl)phthalazin-1-yl)pyrrolidin-3-yl)acetamide

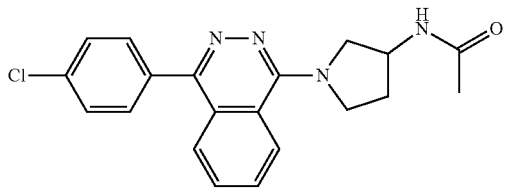 [SMILES: CC(=O)NC1CCN(c2nnc(-c3ccc(Cl)cc3)c3ccccc23)C1]

1H NMR (500 MHz, MeOD): 8.41 (d, 1H), 7.87 (m, 3H), 7.62 (d, 2H), 7.57 (d, 2H), 4.52 (t, 1H), 4.21 (d, 1H), 4.11 (m, 1H), 4.00 (m, 1H), 3.80 (m, 1H), 2.31 (m, 1H), 2.09 (m, 1H), 1.96 (s, 3H)

Example 46: Preparation of 1-(4-(4-chlorophenyl) phthalazin-1-yl)-N-methylpyrrolidin-3-amine hydrochloride

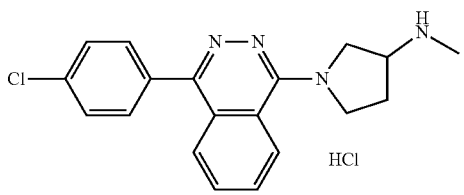 [SMILES: CNC1CCN(c2nnc(-c3ccc(Cl)cc3)c3ccccc23)C1 ; Cl]

1H NMR (500 MHz, MeOD): 8.76 (d, 1H), 8.15 (m, 3H), 7.71 (m, 4H), 4.52-4.17 (m, 6H), 2.89 (s, 3H), 2.69 (m, 1H), 2.49 (m, 1H)

Hereinafter, a compound of Example 47 was produced in the same manner as in Example 31, except that reactants corresponding to the chemical structure of the compound to be produced were used.

Example 47: Preparation of (S)-2-amino-1-(4-(4-(4-chlorophenyl)phthalazin-1-yl)piperazin-1-yl)-3-methylbutan-1-one hydrochloride

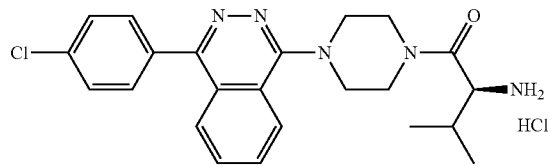

1H NMR (500 MHz, MeOD): 8.53 (d, 1H), 8.29 (t, 1H), 8.20 (m, 2H), 7.76 (m, 4H), 4.43 (d, 1H), 4.12 (d, 1H), 3.99-3.88 (m, 7H), 2.27 (m, 1H), 1.16 (d, 3H), 1.07 (d, 3H)

Example 48: Preparation of (4-(4-(4-chlorophenyl) phthalazin-1-yl)-5,6-dihydropyridin-1(2H)-yl)(cyclopropyl)methanone

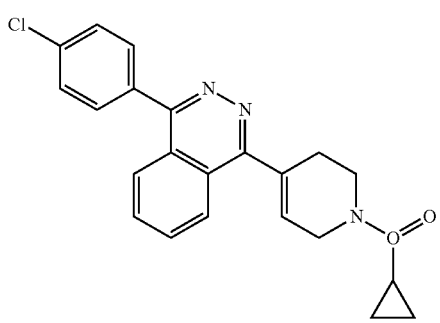

Step 1) Preparation of tert-butyl 4-(4-chlorophthalazin-1-yl)-5,6-dihydropyridin-1(2H)-carboxylate 1,4-Diclophthalazine (0.30 g, 0.97 mmol), Pd (PPh$_3$)$_4$ (0.05 g, 0.10 mmol), tert-butyl 4-(4,4,5,5-tetramethyl-1,3,2-dioxaborolan-2-yl)-3,6-dihydropyridin-1(2H)-carboxylate (0.37 g, 1.21 mmol) was dissolved in dioxane (6 mL) and 2N Na$_2$CO$_3$ aqueous solution. The reaction solution was reacted at 120° C. for 60 minutes using a microwave organic synthesizer. After the termination of the reaction was confirmed by TLC, water (5 mL) was added to the reaction and extracted twice with ethyl acetate (5 mL). The organic layer was dried over MgSO$_4$ and then concentrated under reduced pressure. The resulting residue was separated and purified by chromatography to obtain the desired title compound (0.11 g, 18.7%).

Step 2) Preparation of tert-butyl 4-(4-(4-chlorophenyl)phthalazin-1-yl)-5,6-dihydropyridin-1(2H)-carboxylate The intermediate (0.11 g, 0.32 mmol) obtained in the above step 1, Pd(PPh$_3$)$_4$(0.05 g, 0.03 mmol) and (4-chlorophenyl)boronic acid (0.06 g, 0.36 mmol) were dissolved in dioxane (5 mL) and 2N Na$_2$CO$_3$ aqueous solution. The reaction solution was reacted at 120° C. for 30 minutes using a microwave organic synthesizer. After the termination of the reaction was confirmed by TLC, water (5 mL) was added to the reaction and extracted twice with ethyl acetate (5 mL). The organic layer was dried over MgSO$_4$ and then concentrated under reduced pressure. The resulting residue was separated and purified by chromatography to obtain the desired title compound (0.10 g, 74.5%).

Step 3) Preparation of 1-(4-chlorophenyl)-4-(1,2,3, 6-tetrahydropyridin-4-yl) phthalazine The intermediate (0.10 g, 0.24 mmol) obtained in the above step 2 was dissolved in dichloromethane (3 mL), and then trifluoroacetic acid (0.50 mL) was added thereto. The reaction solution was stirred at room temperature for 4 hours, and then the termination of the reaction was confirmed by TLC. The reaction mixture was washed with a saturated aqueous solution of NaHCO$_3$, and then concentrated under reduced pressure. The resulting residue was washed with dichloromethane and n-hexane to obtain the desired compound (0.07 g, 91.8%).

Step 4) Preparation of (4-(4-(4-chlorophenyl)phthalazin-1-yl)-5,6-dihydropyridin-I (2H)-yl)(cyclopropyl)methanone The intermediate (0.03 g, 0.09 mmol) obtained in the above step 3 and triethylamine (0.02 mL, 0.11 mmol) were dissolved in dichloromethane (2 mL), and then cyclopropanecarbonyl chloride (0.01 mL, 0.11 mmol) was added thereto. The reaction solution was stirred at room temperature for 1 hour, and the termination of the reaction was confirmed by TLC. Water (5 mL) was added to the reaction and extracted twice with dichloromethane (2 mL). The resulting residue was separated and purified by chromatography to obtain the desired title compound (0.02 g, 55.0%).

1H NMR (500 MHz, CDCl$_3$): 8.30 (d, 1H), 8.06 (d, 1H), 7.90 (t, 2H), 7.72 (d, 2H), 7.56 (d, 2H), 6.20 (s, 1H), 4.54-4.44 (m, 2H), 4.07-4.01 (m, 2H), 3.02-2.85 (m, 2H), 1.90-1.83 (m, 1H), 1.09 (m, 2H), 0.85 (m, 2H)

Hereinafter, compounds of Examples 49 and 50 were each produced in the same manner as in Example 12, except that reactants corresponding to the chemical structure of the compound to be produced were used.

Example 49: Preparation of 1-(4-chlorophenyl)-4-(1-(cyclopropylsulfonyl)-1,2,3,6-tetrahydropyridin-4-yl)phthalazine

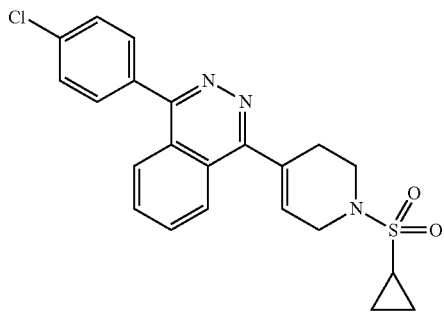 [SMILES: O=S(=O)(C1CC1)N1CC=C(c2nnc(-c3ccc(Cl)cc3)c3ccccc23)CC1]

1H NMR (500 MHz, CDCl₃): 8.27 (d, 1H), 8.06 (d, 1H), 7.92 (t, 1H), 7.88 (t, 1H), 7.72 (d, 2H), 7.56 (d, 2H), 6.17 (s, 1H), 4.20 (d, 2H), 3.74 (t, 2H), 3.00 (d, 2H), 2.41 (t, 1H), 1.28 (m, 2H), 1.07 (m, 2H)

Example 50: Preparation of 1-(4-chlorophenyl)-4-(4-(cyclopropylmethyl)piperazin-1-yl)phthalazine

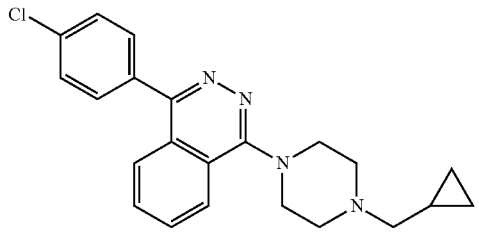 [SMILES: Clc1ccc(-c2nnc(N3CCN(CC4CC4)CC3)c3ccccc23)cc1]

1H NMR (500 MHz, MeOD): 8.50 (m, 1H), 8.29 (m, 1H), 8.22 (m, 2H), 7.78 (m, 4H), 3.95 (br, 4H), 3.74 (br, 3H), 3.67 (br, 2H), 3.66 (br, 4H)

Hereinafter, compounds of Examples 51 and 52 were each produced in the same manner as in Example 31, except that reactants corresponding to the chemical structure of the compound to be produced were used.

Example 51: Preparation of (R)-(4-(4-(4-chlorophenyl)phthalazin-1-yl)piperazin-1-yl)(pyrrolidin-2-yl)methanone hydrochloride

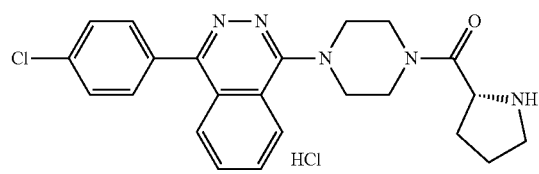 [SMILES: O=C([C@H]1CCCN1)N1CCN(c2nnc(-c3ccc(Cl)cc3)c3ccccc23)CC1 ; Cl]

1H NMR (500 MHz, MeOD): 8.56 (d, 1H), 8.33 (t, 1H), 8.22 (m, 2H), 7.79 (m, 4H), 3.93 (m, 7H), 3.46 (m, 2H), 3.39 (m, 2H), 2.59 (m, 1H), 2.11 (m, 3H), 1.17 (t, 1H)

Example 52: Preparation of (1-aminocyclopropyl)(4-(4-(4-chlorophenyl)phthalazin-1-yl)piperazin-1-yl)methanone hydrochloride

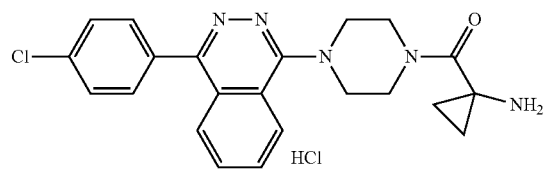 [SMILES: NC1(C(=O)N2CCN(c3nnc(-c4ccc(Cl)cc4)c4ccccc34)CC2)CC1 ; Cl]

1H NMR (500 MHz, MeOD): 8.24 (d, 1H), 7.93 (m, 3H), 7.67 (d, 2H), 7.60 (d, 2H), 3.64 (m, 4H), 2.98 (m, 4H), 2.50 (d, 2H), 0.67 (m, 2H), 0.24 (m, 2H)

Hereinafter, the compounds of Examples 53 to 55 were each produced in the same manner as in Example 12, except that reactants corresponding to the chemical structure of the compound to be produced were used. At this time, when an amine group was present in the compound to be produced, the protective group (Boc) was introduced and finally an elimination reaction of the protective group was performed as in Step 3 of Example 31.

Example 53: Preparation of N1-(4-(4-chlorophenyl)phthalazin-1-yl)-N1,N2-dimethylethane-1,2-diamine

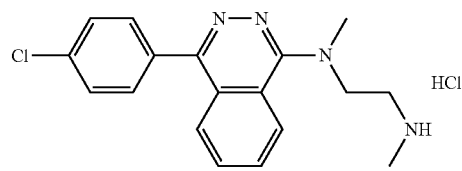 [SMILES: CNCCN(C)c1nnc(-c2ccc(Cl)cc2)c2ccccc12 ; Cl]

1H NMR (500 MHz, MeOD): 8.67 (d, 1H), 8.30 (t, 1H), 8.19 (m, 2H), 7.78 (m, 4H), 4.10 (t, 2H), 3.57 (s, 3H), 3.54 (t, 2H), 2.82 (s, 3H)

Example 54: Preparation of 1-(4-(4-chlorophenyl)phthalazin-1-yl)-N-ethylpyrrolidin-3-amine hydrochloride

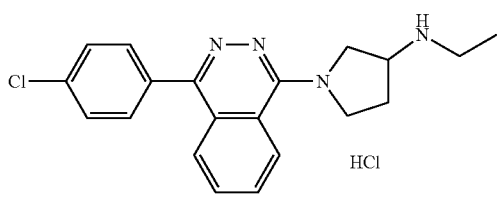 [SMILES: CCNC1CCN(c2nnc(-c3ccc(Cl)cc3)c3ccccc23)C1 ; Cl]

1H NMR (500 MHz, MeOD): 8.77 (d, 1H), 8.22 (m, 1H), 8.17 (t, 1H), 8.13 (m, 1H), 7.70 (m, 4H), 4.52 (br, 1H), 4.40 (br, 1H), 4.27 (m, 3H), 3.20 (q, 2H), 2.70 (m, 1H), 2.51 (m, 1H), 1.42 (t, 3H)

Example 55: Preparation of N1-(4-(4-chlorophenyl)phthalazin-1-yl)-N1,N3-dimethylpropane-1,3-diamine hydrochloride

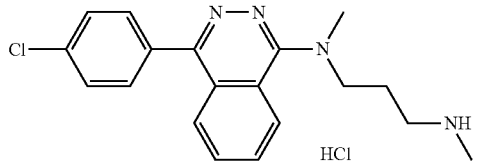 [SMILES: CNCCCN(C)c1nnc(-c2ccc(Cl)cc2)c2ccccc12 ; Cl]

1H NMR (500 MHz, MeOD): 8.62 (d, 1H), 8.24 (t, 1H), 8.14 (m, 2H), 7.75 (d, 2H), 7.72 (d, 2H), 3.96 (m, 2H), 3.59 (s, 3H), 3.19 (t, 2H), 2.76 (s, 3H), 2.35 (m, 2H)

Example 56: Preparation of (4-(4-(4-chlorophenyl)phthalazin-1-yl)piperidin-1-yl)(cyclopropyl)methanone

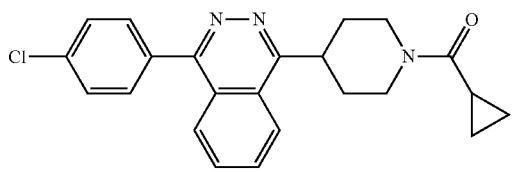

Step 1) Preparation of tert-butyl 4-(4-(4-chlorophenyl)phthalazin-1-yl)piperidine-1-carboxylate The intermediate tert-butyl 4-(4-(4-chlorophenyl)phthalazin-1-yl)-5,6-dihydropyridin-1(2H)-carboxylate (0.07 g, 0.20 mmol) obtained in the step 2 of Example 48 was dissolved in methanol (1 mL) and then $PtO_2$ (5 mg, cat.) was added thereto. Then, the atmosphere was replaced with hydrogen gas, followed by stirring at room temperature, and the termination of the reaction was confirmed by TLC. The reaction product was separated by a PLC plate to obtain the desired compound (0.03 g, 42.5%).

Step 2) Preparation of (4-(4-(4-chlorophenyl)phthalazin-1-yl)piperidin-1-yl)(cyclopropyl)methanone The desired compound (0.01 g, 50.5%) was prepared in the same manner as in the steps 3 and 4 of Example 48, except for using the intermediate (0.03 g, 0.07 mmol) obtained in the above step 1 as a starting material.

1H NMR (500 MHz, MeOD): 8.54 (d, 1H), 8.08 (t, 1H), 8.05 (d, 1H), 8.00 (t, 1H), 7.69 (d, 2H), 7.62 (d, 2H), 4.70 (d, 1H), 4.57 (d, 1H), 4.09 (m, 1H), 3.53 (t, 1H), 3.03 (t, 1H), 2.19 (m, 2H), 2.06 (m, 2H), 0.92 (m, 2H), 0.85 (m, 2H)

Hereinafter, the compound of Example 57 was produced in the same manner as in Example 12, except that reactants corresponding to the chemical structure of the compound to be produced were used. At this time, when an amine group was present in the compound to be produced, a protecting group (Boc) was introduced and finally an elimination reaction of the protective group was performed as in the step 3 of Example 31.

Example 57: Preparation of (R)-1-(4-(4-chlorophenyl)phthalazin-1-yl)-N-methylpiperidin-3-amine hydrochloride

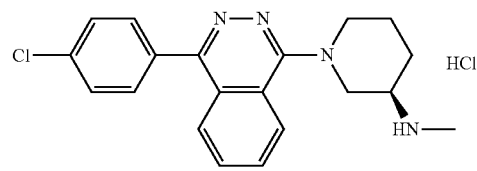 [SMILES: CN[C@@H]1CCCN(c2nnc(-c3ccc(Cl)cc3)c3ccccc23)C1 ; Cl]

1H NMR (500 MHz, MeOD): 8.22 (d, 1H), 7.97 (t, 1H), 7.89 (m, 2H), 7.62 (d, 2H), 7.56 (d, 2H), 4.00 (m, 1H), 3.70 (d, 1H), 3.15 (m, 3H), 2.66 (s, 3H), 2.19 (m, 1H), 2.00 (m, 1H), 1.90 (m, 1H), 1.61 (m, 1H)

Hereinafter, the compounds of Examples 58 to 60 were produced in the same manner as in Example 31, except that reactants corresponding to the chemical structure of the compound to be produced were each used.

Example 58: Preparation of (1-aminocyclopentyl)(4-(4-(4-chlorophenyl)phthalazin-1-yl)piperazin-1-yl)methanone hydrochloride

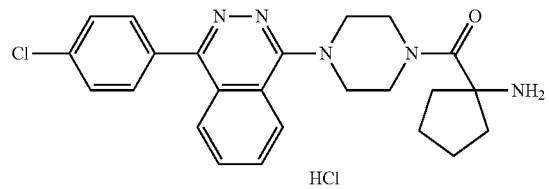 [SMILES: NC1(C(=O)N2CCN(c3nnc(-c4ccc(Cl)cc4)c4ccccc34)CC2)CCCC1 ; Cl]

1H NMR (500 MHz, MeOD): 8.57 (d, 1H), 8.33 (m, 1H), 8.23 (m, 2H), 7.80 (d, 2H), 7.77 (d, 2H), 3.94 (m, 8H), 2.43 (m, 2H), 2.07 (m, 7H)

Example 59: Preparation of (S)-(4-(4-(4-chlorophenyl)phthalazin-1-yl)piperazin-1-yl)(pyrrolidin-2-yl)methanone hydrochloride

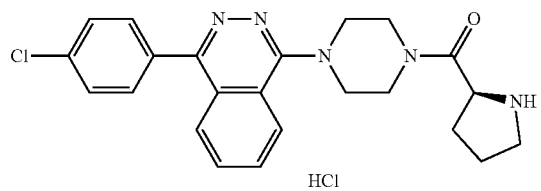 [SMILES: O=C([C@@H]1CCCN1)N1CCN(c2nnc(-c3ccc(Cl)cc3)c3ccccc23)CC1 ; Cl]

1H NMR (500 MHz, MeOD): 8.59 (d, 1H), 8.33 (m, 1H), 8.23 (m, 2H), 7.79 (m, 4H), 4.08 (m, 1H), 3.95 (m, 7H), 3.40 (m, 2H), 2.59 (m, 1H), 2.10 (m, 4H)

Example 60: Preparation of (2S,3S)-2-amino-1-(4-(4-(4-chlorophenyl)phthalazin-1-yl)piperazin-1-yl)-3-methylpentan-1-one hydrochloride

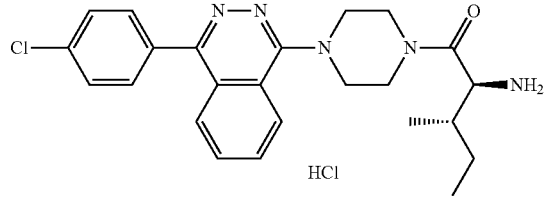 [SMILES: CC[C@H](C)[C@H](N)C(=O)N1CCN(c2nnc(-c3ccc(Cl)cc3)c3ccccc23)CC1 ; Cl]

1H NMR (500 MHz, MeOD): 8.58 (d, 1H), 8.34 (m, 1H), 8.23 (s, 2H), 7.80 (d, 2H), 7.75 (d, 2H), 4.49 (m, 1H), 4.16 (m, 1H), 4.06 (t, 1H), 3.96 (m, 4H), 3.87 (m, 2H), 2.00 (m, 1H), 1.61 (m, 1H), 1.29 (m, 1H), 1.14 (m, 3H), 1.01 (m, 3H)

Hereinafter, the compounds of Examples 61 to 64 were produced in the same manner as in Example 56, except that reactants corresponding to the chemical structure of the compound to be produced were each used. At this time, when an amine group was present in the compound to be produced, the protecting group (Boc) was introduced and finally an elimination reaction of protective group was performed as in Step 3 of Example 31.

Example 61: Preparation of (S)-2-amino-1-(4-(4-(4-chlorophenyl)phthalazin-1-yl)piperidin-1-yl)-3-methylbutan-1-one hydrochloride

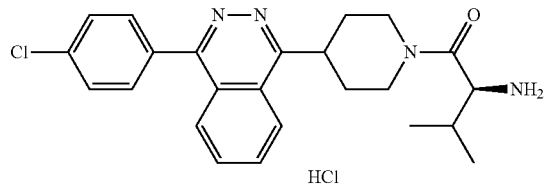 [SMILES: CC(C)[C@H](N)C(=O)N1CCC(c2nnc(-c3ccc(Cl)cc3)c3ccccc23)CC1 ; Cl]

1H NMR (500 MHz, MeOD): 8.96 (d, 1H), 8.53 (t, 1H), 8.41 (d, 1H), 8.36 (t, 1H), 7.90 (d, 2H), 7.82 (d, 2H), 4.80 (m, 1H), 4.50 (d, 1H), 4.42 (d, 1H), 4.34 (t, 1H), 4.23 (t, 1H), 3.60 (m, 2H), 3.17 (m, 1H), 2.26 (m, 3H), 2.10 (m, 1H), 1.17 (m, 3H), 1.06 (m, 3H)

Example 62: Preparation of (S)-(4-(4-(4-chlorophenyl)phthalazin-1-yl)piperidin-1-yl)(pyrrolidin-2-yl)methanone hydrochloride

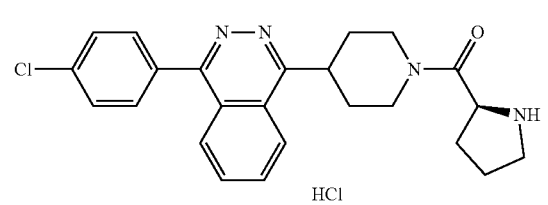 [SMILES: O=C([C@@H]1CCCN1)N1CCC(c2nnc(-c3ccc(Cl)cc3)c3ccccc23)CC1 ; Cl]

1H NMR (500 MHz, MeOD): 8.95 (d, 1H), 8.53 (t, 1H), 8.41 (d, 1H), 8.37 (t, 1H), 7.79 (d, 2H), 7.81 (d, 2H), 4.75 (m, 2H), 4.34 (m, 1H), 4.14 (m, 1H), 3.59 (m, 1H), 3.45 (m, 2H), 3.20 (m, 1H), 2.61 (m, 1H), 2.27-2.00 (m, 7H)

Example 63: Preparation of (2S,3S)-2-amino-1-(4-(4-(4-chlorophenyl)phthalazin-1-yl)piperidin-1-yl)-3-methylpentan-1-one hydrochloride

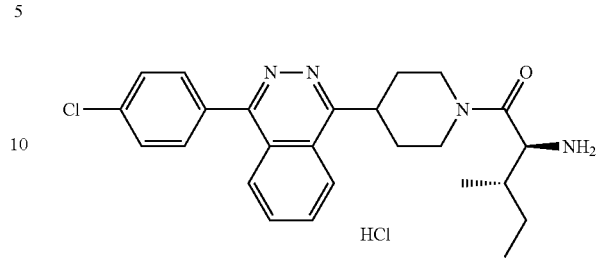

1H NMR (500 MHz, MeOD): 8.96 (d, 1H), 8.53 (t, 1H), 8.41 (d, 1H), 8.36 (t, 1H), 7.90 (d, 2H), 7.82 (d, 2H), 4.78 (m, 1H), 4.51 (m, 1H), 4.44 (m, 1H), 4.35 (m, 1H), 4.21 (m, 1H), 3.61 (m, 1H), 3.19 (m, 1H), 2.27 (m, 3H), 1.98 (m, 2H), 1.60 (m, 1H), 1.27 (m, 1H), 1.13 (m, 3H), 1.01 (m, 3H)

Example 64: Preparation of 2-amino-1-(4-(4-(4-chlorophenyl)phthalazin-1-yl)piperidin-1-yl)-2-methylpropan-1-one hydrochloride

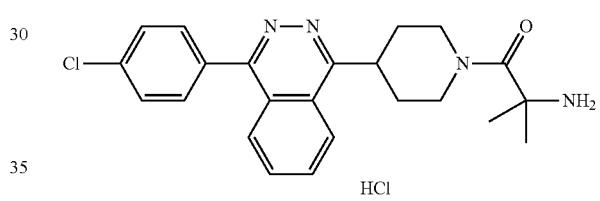

1H NMR (500 MHz, MeOD): 8.72 (d, 1H), 8.33 (t, 1H), 8.26 (d, 1H), 8.20 (t, 1H), 7.78 (d, 2H), 7.75 (d, 2H), 4.56 (m, 1H), 4.23 (t, 1H), 3.44 (m, 3H), 2.23 (d, 2H), 2.09 (d, 2H), 1.74 (s, 6H)

Hereinafter, the compounds of Examples 65 and 66 were each produced in the same manner as in Example 32, except that reactants corresponding to the chemical structure of the compound to be produced were used.

Example 65: Preparation of ethyl 2-(4-(4-(4-chlorophenyl)phthalazin-1-yl)piperazin-1-yl)acetate

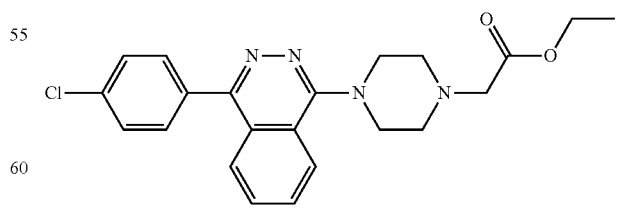

1H NMR (500 MHz, CDCl₃): 8.11 (d, 1H), 7.95 (d, 1H), 7.82 (t, 1H), 7.76 (d, 1H), 7.68 (d, 2H), 7.50 (d, 2H), 4.22 (q, 2H), 3.67 (m, 4H), 3.36 (m, 2H), 2.92 (s, 4H), 1.31 (t, 3H)

Example 66: Preparation of ethyl 2-(4-(4-(4-chlorophenyl)phthalazin-1-yl)piperazin-1-yl)-2-methylpropanoate

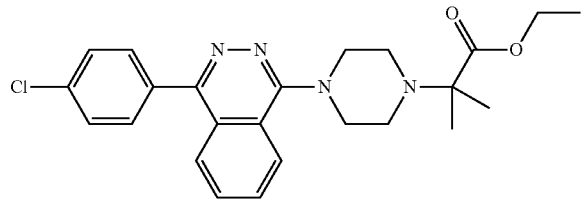 [SMILES: CCOC(=O)C(C)(C)N1CCN(c2nnc(-c3ccc(Cl)cc3)c3ccccc23)CC1]

1H NMR (500 MHz, CDCl₃): 8.13 (d, 1H), 7.96 (d, 1H), 7.82 (t, 1H), 7.76 (d, 1H), 7.68 (d, 2H), 7.51 (d, 2H), 4.34 (q, 2H), 3.61 (m, 4H), 2.93 (m, 4H), 1.41 (s, 6H), 1.32 (t, 3H)

Hereinafter, the compound of Example 67 was produced in the same manner as in Example 12, except that reactants corresponding to the chemical structure of the compound to be produced were used.

Example 67: Preparation of 1-(4-benzyl-1,4-diazepan-1-yl)-4-(4-chlorophenyl)phthalazine

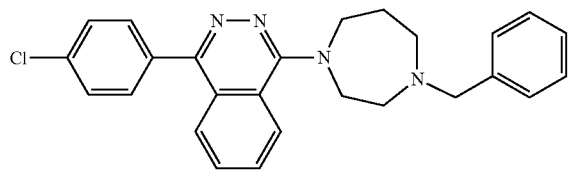 [SMILES: Clc1ccc(-c2nnc(N3CCCN(Cc4ccccc4)CC3)c3ccccc23)cc1]

1H NMR (500 MHz, MeOD): 8.23 (d, 1H), 7.90 (m, 2H), 7.86 (d, 1H), 7.64 (m, 5H), 7.37 (d, 2H), 7.26 (t, 2H), 3.96 (m, 4H), 3.73 (s, 2H), 2.98 (m, 2H), 2.84 (m, 2H), 2.15 (m, 2H)

Hereinafter, the compound of Example 68 was produced in the same manner as in Example 32, except that reactants corresponding to the chemical structure of the compound to be produced were used.

Example 68: Preparation of 2-(4-(4-(4-chlorophenyl)phthalazin-1-yl)piperazin-1-yl)acetic acid

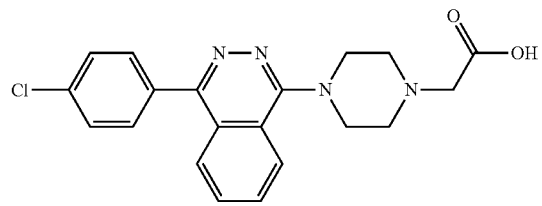 [SMILES: O=C(O)CN1CCN(c2nnc(-c3ccc(Cl)cc3)c3ccccc23)CC1]

1H NMR (500 MHz, MeOD): 8.28 (d, 1H), 8.03 (t, 1H), 7.98 (m, 2H), 7.67 (d, 2H), 7.61 (d, 2H), 3.83 (m, 4H), 3.68 (m, 2H), 3.56 (m, 4H)

Hereinafter, the compounds of Examples 69 to 81 were each produced in the same manner as in Example 31, except that reactants corresponding to the chemical structure of the compound to be produced were used.

Example 69: Preparation of (S)-2-amino-1-(4-(4-(4-chlorophenyl)phthalazin-1-yl)-2,2-dimethylpiperazin-1-yl)-3-methylbutan-1-one hydrochloride

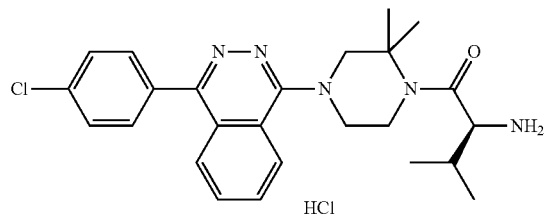 [SMILES: CC(C)[C@H](N)C(=O)N1CCN(c2nnc(-c3ccc(Cl)cc3)c3ccccc23)CC1(C)C ; Cl]

1H NMR (500 MHz, MeOD): 8.58 (m, 1H), 8.13-8.05 (m, 3H), 7.71 (m, 4H), 4.37 (m, 2H), 4.06 (m, 4H), 2.29 (m, 1H), 1.65 (m, 6H), 1.16 (d, 3H), 1.05 (d, 3H), 0.95 (t, 1H)

Example 70: Preparation of (R)-2-amino-1-(4-(4-(4-chlorophenyl)phthalazin-1-yl)-2-methylpiperazin-1-yl)-2-methylpropan-1-one hydrochloride

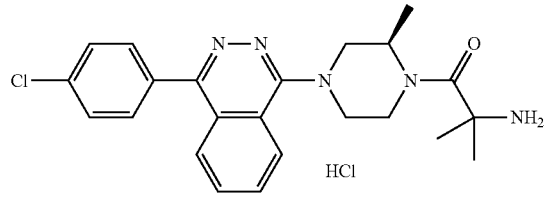 [SMILES: C[C@@H]1CN(c2nnc(-c3ccc(Cl)cc3)c3ccccc23)CCN1C(=O)C(C)(C)N ; Cl]

1H NMR (500 MHz, MeOD): 8.38 (m, 1H), 8.06 (m, 3H), 7.68 (m, 4H), 4.00 (m, 3H), 3.44 (m, 4H), 1.74 (s, 6H), 1.56 (m, 3H)

Example 71: Preparation of (S)-2-amino-1-((R)-4-(4-(4-chlorophenyl)phthalazin-1-yl)-2-methylpiperazin-1-yl)-3-methylbutan-1-one hydrochloride

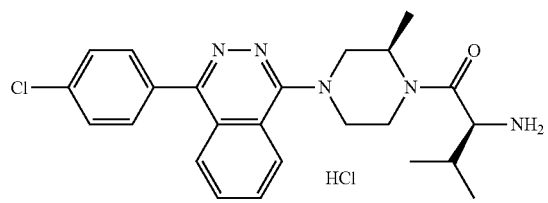 [SMILES: CC(C)[C@H](N)C(=O)N1CCN(c2nnc(-c3ccc(Cl)cc3)c3ccccc23)C[C@H]1C ; Cl]

1H NMR (500 MHz, MeOD): 8.50 (m, 1H), 8.26 (m, 1H), 8.17 (m, 2H), 7.74 (m, 4H), 4.33 (d, 1H), 4.10 (m, 2H), 3.56 (m, 4H), 2.26 (m, 1H), 1.62 (m, 1H), 1.50 (d, 2H), 1.15 (d, 3H), 1.05 (d, 3H)

Example 72: Preparation of (S)-2-amino-1-(4-(4-(4-chlorophenyl)phthalazin-1-yl)-2-methylpiperazin-1-yl)-2-methylpropan-1-one hydrochloride

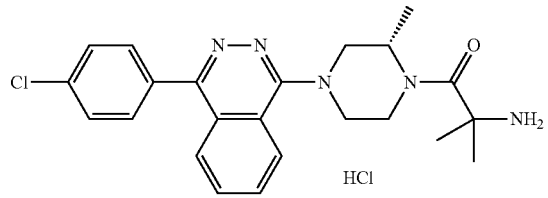 [SMILES: C[C@H]1CN(c2nnc(-c3ccc(Cl)cc3)c3ccccc23)CCN1C(=O)C(C)(C)N ; Cl]

1H NMR (500 MHz, MeOD): 8.34 (d, 1H), 8.04 (t, 1H), 7.99 (m, 2H), 7.66 (d, 2H), 7.63 (d, 2H), 3.98 (d, 1H), 3.85 (d, 1H), 3.36-3.32 (m, 5H), 1.75 (s, 6H), 1.58 (m, 3H)

Example 73: Preparation of (S)-2-amino-1-((S)-4-(4-(4-chlorophenyl)phthalazin-1-yl)-2-methylpiperazin-1-yl)-3-methylbutan-1-one hydrochloride

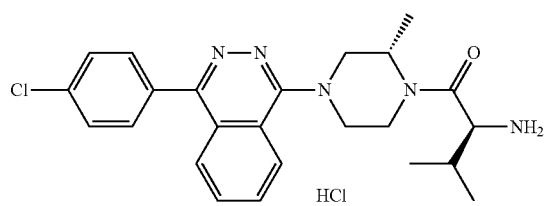 [SMILES: CC(C)[C@H](N)C(=O)N1CCN(c2nnc(-c3ccc(Cl)cc3)c3ccccc23)C[C@@H]1C ; Cl]

1H NMR (500 MHz, MeOD): 8.53 (d, 1H), 8.29 (d, 1H), 8.19 (m, 2H), 7.75 (m, 4H), 4.51-4.34 (m, 1H), 4.20 (m, 1H), 4.09 (m, 2H), 3.58 (m, 1H), 3.45 (m, 1 h), 2.27 (m, 1H), 1.67 (m, 1H), 1.53 (m, 2H), 1.16 (d, 3H), 1.07 (d, 3H)

Example 74: Preparation of (S)-2-amino-1-(4-(4-(4-chlorophenyl)phthalazin-1-yl)-3-methylpiperazin-1-yl)-2-methylpropan-1-one hydrochloride

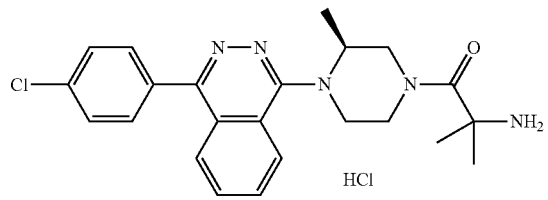 [SMILES: C[C@H]1CN(C(=O)C(C)(C)N)CCN1c1nnc(-c2ccc(Cl)cc2)c2ccccc12 ; Cl]

1H NMR (500 MHz, MeOD): 8.45 (d, 1H), 8.13-8.05 (m, 3H), 7.73 (m, 4H), 4.26 (m, 3H), 3.79 (m, 4H), 1.78 (d, 3H), 1.74 (d, 3H), 1.35 (m, 3H)

Example 75: Preparation of (S)-2-amino-1-((S)-4-(4-(4-chlorophenyl)phthalazin-1-yl)-3-methylpiperazin-1-yl)-3-methylbutan-1-one hydrochloride

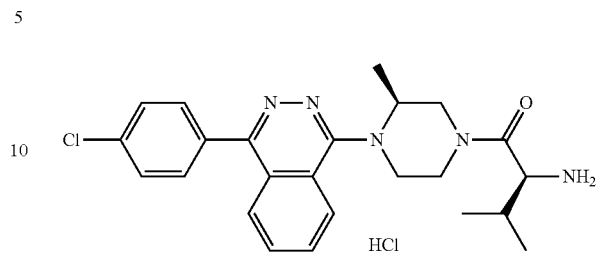

1H NMR (500 MHz, MeOD): 8.44 (d, 1H), 8.15 (m, 3H), 7.74 (m, 4H), 4.38 (m, 2H), 4.04 (m, 1H), 3.78 (m, 3H), 2.32 (m, 1H), 1.41-1.25 (m, 3H), 1.15 (d, 3H), 1.04 (d, 3H)

Example 76: Preparation of (S)-2-amino-1-(4-(4-(4-chlorophenyl)phthalazin-1-yl)piperazin-1-yl)-3-(1H-imidazol-4-yl)propan-1-one dihydrochloride

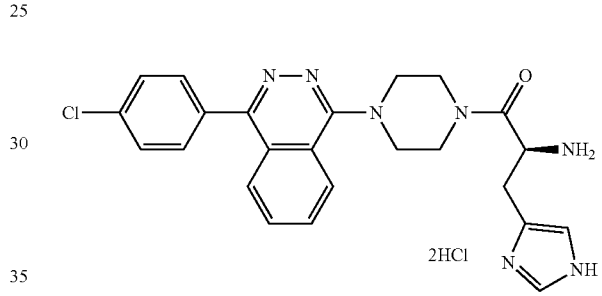

1H NMR (500 MHz, MeOD): 8.78 (m, 1H), 8.38 (m, 1H), 8.05 (m, 3H), 7.68 (m, 4H), 7.48 (d, 1H), 4.05-3.85 (m, 4H), 3.64 (m, 4H), 3.36 (m, 2H)

Example 77: Preparation of 2-amino-1-(4-(4-(4-chlorophenyl)phthalazin-1-yl)piperazin-1-yl)-3,3-dimethylbutan-1-one hydrochloride

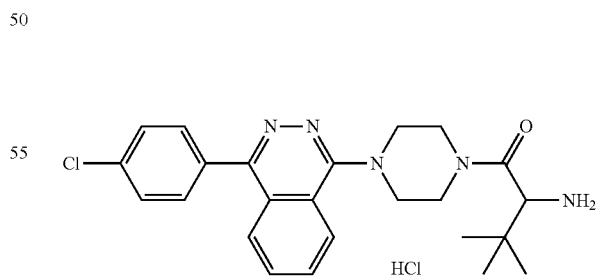

1H NMR (500 MHz, MeOD): 8.52 (d, 1H), 8.26 (t, 1H), 8.17 (m, 2H), 7.75 (m, 4H), 4.43 (s, 1H), 4.21 (d, 1H), 4.10 (m, 1H), 3.94 (m, 3H), 3.74 (m, 3H), 1.16 (s, 9H)

Example 78: Preparation of (4-(4-(4-chlorophenyl)phthalazin-1-yl)piperazin-1-yl)(piperidin-2-yl)methanone hydrochloride

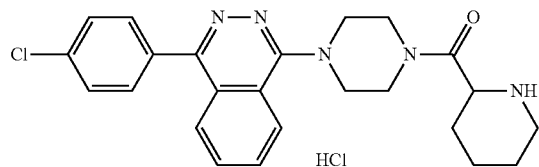 [SMILES: O=C(C1CCCCN1)N1CCN(c2nnc(-c3ccc(Cl)cc3)c3ccccc23)CC1 ; Cl]

1H NMR (500 MHz, MeOD): 8.40 (m, 1H), 8.12-8.06 (m, 3H), 7.70 (m, 4H), 4.41 (d, 1H), 4.05 (m, 1H), 3.89-3.74 (m, 7H), 3.44 (m, 2H), 3.08 (m, 1H), 2.23 (d, 1H), 2.00-1.91 (m, 2H), 1.75-1.73 (m, 3H)

Example 79: Preparation of (S)-2-amino-3-(benzyloxy)-1-(4-(4-(4-chlorophenyl)phthalazin-1-yl)piperazin-1-yl)propan-1-one hydrochloride

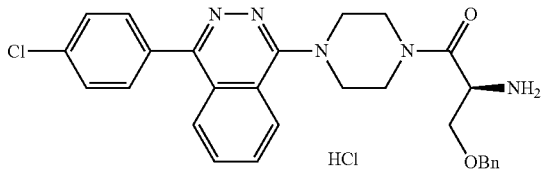 [SMILES: N[C@@H](COCc1ccccc1)C(=O)N1CCN(c2nnc(-c3ccc(Cl)cc3)c3ccccc23)CC1 ; Cl]

1H NMR (500 MHz, MeOD): 8.44-8.40 (m, 1H), 8.18-8.11 (m, 3H), 7.72 (m, 4H), 7.39 (m, 4H), 4.68 (d, 1H), 4.61 (d, 1H), 3.95 (m, 1H), 3.85-3.77 (m, 9H)

Example 80: Preparation of (S)-2-amino-1-(4-(4-(4-chlorophenyl)phthalazin-1-yl)piperazin-1-yl)-2-phenylethanone hydrochloride

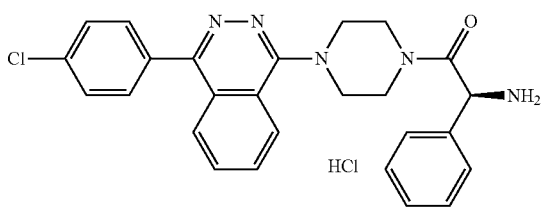 [SMILES: N[C@H](C(=O)N1CCN(c2nnc(-c3ccc(Cl)cc3)c3ccccc23)CC1)c1ccccc1 ; Cl]

1H NMR (500 MHz, MeOD): 8.30 (d, 1H), 8.05 (m, 3H), 7.68 (m, 4H), 7.54 (m, 5H), 5.59 (s, 1H), 4.01 (m, 2H), 3.80 (m, 1H), 3.78 (m, 1H), 3.67 (m, 3H), 3.15 (m, 1H)

Example 81: Preparation of (S)-5-(4-(4-(4-chlorophenyl)phthalazin-1-yl)piperazine-1-carbonyl)piperazin-2-one hydrochloride

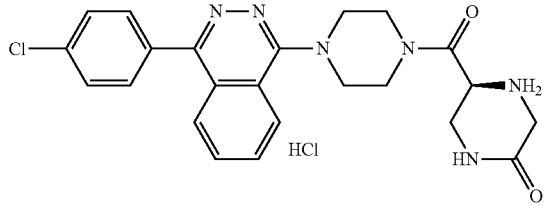 [SMILES: O=C1CN[C@H](C(=O)N2CCN(c3nnc(-c4ccc(Cl)cc4)c4ccccc34)CC2)CN1 ; Cl]

1H NMR (500 MHz, MeOD): 8.51 (d, 1H), 8.27 (t, 1H), 8.18 (m, 2H), 7.77 (d, 2H), 7.75 (d, 2H), 4.98 (m, 1H), 4.09 (m, 1H), 3.97-3.79 (m, 1 OH), 3.59 (m, 1H)

Hereinafter, the compound of Example 82 was produced in the same manner as in Example 32, except that reactants corresponding to the chemical structure of the compound to be produced were used.

Example 82: Preparation of 2-(4-(4-(4-chlorophenyl)phthalazin-1-yl)piperazin-1-yl)-2-methylpropanoic acid

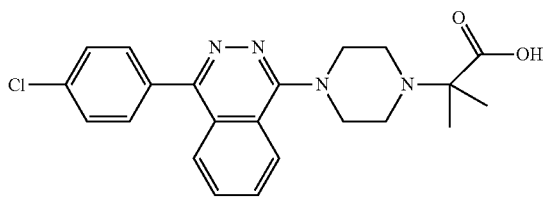 [SMILES: CC(C)(C(=O)O)N1CCN(c2nnc(-c3ccc(Cl)cc3)c3ccccc23)CC1]

1H NMR (500 MHz, MeOD): 8.31 (d, 1H), 8.03 (t, 1H), 7.97 (m, 2H), 7.66 (d, 2H), 7.63 (d, 2H), 3.89 (br, 4H), 3.57 (br, 4H), 1.57 (s, 6H)

Hereinafter, the compounds of Examples 83 to 86 were each produced in the same manner as in Example 31, except that reactants corresponding to the chemical structure of the compound to be produced were used.

Example 83: Preparation of 3-amino-4-(4-(4-(4-chlorophenyl)phthalazin-1-yl)piperazin-1-yl)-4-oxobutanoic acid hydrochloride

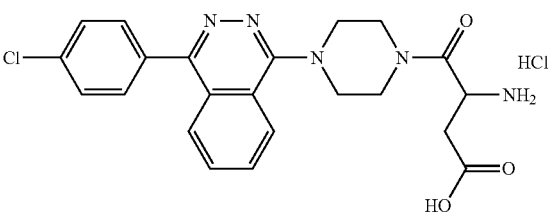 [SMILES: NC(CC(=O)O)C(=O)N1CCN(c2nnc(-c3ccc(Cl)cc3)c3ccccc23)CC1 ; Cl]

1H NMR (500 MHz, MeOD): 8.59 (d, 1H), 8.33 (t, 1H), 8.21 (m, 2H), 7.81 (d, 2H), 7.65 (d, 2H), 4.84 (m, 2H), 4.06 (m, 2H), 4.00-3.91 (m, 6H), 3.02 (m, 1H), 2.87 (m, 1H)

Example 84: Preparation of 4-amino-5-(4-(4-(4-chlorophenyl)phthalazin-1-yl)piperazin-1-yl)-5-oxo-pentanamide hydrochloride

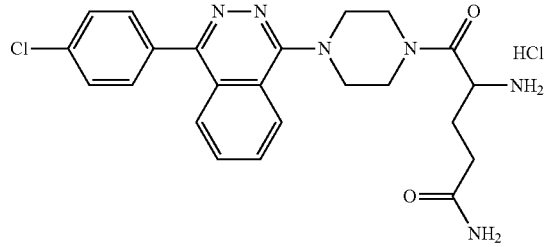 [SMILES: NC(=O)CCC(N)C(=O)N1CCN(c2nnc(-c3ccc(Cl)cc3)c3ccccc23)CC1 ; Cl]

1H NMR (500 MHz, MeOD): 8.58 (d, 1H), 8.33 (m, 1H), 8.23 (m, 2H), 7.69 (d, 2H), 7.74 (d, 2H), 4.62 (md, 1H), 4.04-3.93 (m, 8H), 2.53 (m, 2H), 2.20 (m, 1H), 2.11 (m, 1H)

Example 85: Preparation of 3-amino-4-(4-(4-(4-chlorophenyl)phthalazin-1-yl)piperazin-1-yl)-4-oxobutanamide hydrochloride

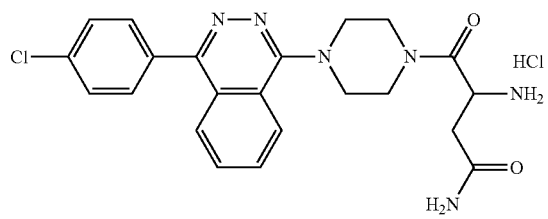 [SMILES: NC(=O)CC(N)C(=O)N1CCN(c2nnc(-c3ccc(Cl)cc3)c3ccccc23)CC1 ; Cl]

1H NMR (500 MHz, MeOD): 8.56 (d, 1H), 8.32 (m, 1H), 8.22 (m, 2H), 7.80 (d, 2H), 7.77 (d, 2H), 4.82 (m, 1H), 4.05 (br, 1H), 3.97 (m, 6H), 2.92 (dd, 1H), 2.77 (dd, 1H)

Example 86: Preparation of 4-amino-5-(4-(4-(4-chlorophenyl)phthalazin-1-yl)piperazin-1-yl)-5-oxo-pentanoic acid hydrochloride

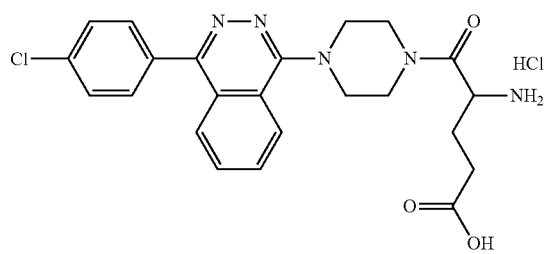 [SMILES: NC(CCC(=O)O)C(=O)N1CCN(c2nnc(-c3ccc(Cl)cc3)c3ccccc23)CC1 ; Cl]

1H NMR (500 MHz, MeOD): 8.58 (d, 1H), 8.33 (m, 1H), 8.23 (m, 2H), 7.76 (m, 4H), 4.65 (s, 1H), 4.05-3.93 (m, 8H), 2.60 (br, 2H), 2.23-2.13 (m, 2H)

Hereinafter, the compounds of Examples 87 to 91 were each produced in the same manner as in Example 12, except that reactants corresponding to the chemical structure of the compound to be produced were used. At this time, when an amine group was present in the compound to be produced, a protecting group (Boc) was introduced and finally an elimination reaction of the protective group was performed as in Step 3 of Example 31.

Example 87: Preparation of 1-(4-chlorophenyl)-4-(tetrahydro-1H-pyrrolo[2,3-c]pyridin-6(2H,7H,7aH)-yl)phthalazine hydrochloride

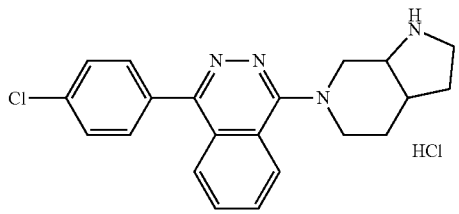 [SMILES: Clc1ccc(-c2nnc(N3CCC4CCNC4C3)c3ccccc23)cc1 ; Cl]

1H NMR (500 MHz, MeOD): 8.56 (d, 1H), 8.28 (t, 1H), 8.18 (m, 2H), 7.78 (d, 2H), 7.74 (d, 2H), 4.11 (m, 2H), 4.00 (m, 2H), 3.81 (t, 1H), 3.62 (m, 1H), 3.45 (m, 1H), 2.95 (m, 1H), 2.43 (m, 1H), 2.33 (m, 2H), 2.16 (m, 1H)

Example 88: Preparation of 1-(4-chlorophenyl)-4-(hexahydropyrrolo[3,4-b]pyrrol-5(1H)-yl)phthalazine hydrochloride

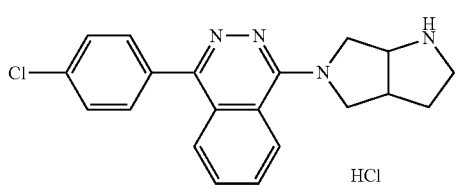 [SMILES: Clc1ccc(-c2nnc(N3CC4CCNC4C3)c3ccccc23)cc1 ; Cl]

1H NMR (500 MHz, MeOD): 8.79 (d, 1H), 8.21 (t, 1H), 8.16 (t, 1H), 8.10 (d, 1H), 7.72 (d, 2H), 7.68 (d, 2H), 4.64 (m, 3H), 4.40 (t, 1H), 4.15 (m, 1H), 3.66 (m, 1H), 3.53 (m, 2H), 2.45 (m, 1H), 2.29 (m, 1H)

Example 89: Preparation of 1-(7-chloro-4-(4-chlorophenyl)phthalazin-1-yl)-N-methylpyrrolidin-3-amine hydrochloride

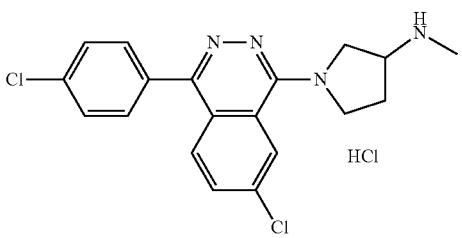 [SMILES: CNC1CCN(c2nnc(-c3ccc(Cl)cc3)c3ccc(Cl)cc23)C1 ; Cl]

1H NMR (500 MHz, MeOD): 8.68 (d, 1H), 8.16 (d, 1H), 8.10 (d, 1H), 7.71 (m, 4H), 4.51 (m, 1H), 4.36 (m, 1H), 4.26 (m, 1H), 4.18 (m, 1H), 4.09 (m, 1H), 2.87 (s, 3H), 2.69 (m, 1H), 2.554 (m, 1H)

Example 90: Preparation of 1-(6-chloro-4-(4-chlorophenyl)phthalazin-1-yl)-N-methylpyrrolidin-3-amine hydrochloride

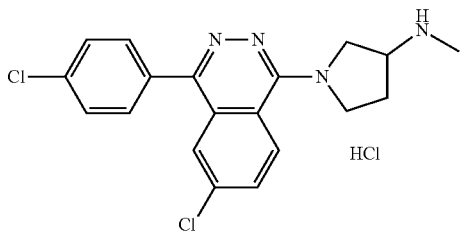 [SMILES: CNC1CCN(c2nnc(-c3ccc(Cl)cc3)c3cc(Cl)ccc23)C1 ; Cl]

1H NMR (500 MHz, MeOD): 8.75 (d, 1H), 8.18 (d, 1H), 8.01 (s, 1H), 7.70 (m, 4H), r4.51 (br, 1H), 4.38 (m, 2H), 4.26-4.19 (m, 2H), 2.88 (s, 3H), 2.70 (m, 1H), 2.51 (m, 1H)

Example 91: Preparation of 1-(4-(4-chlorophenyl)-6-fluorophthalazin-1-yl)-N-methylpyrrolidin-3-amine hydrochloride

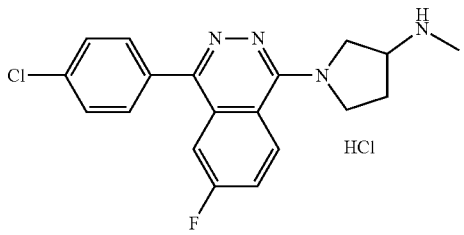 [SMILES: CNC1CCN(c2nnc(-c3ccc(Cl)cc3)c3cc(F)ccc23)C1 ; Cl]

1H NMR (500 MHz, MeOD): 8.85 (dd, 1H), 7.98 (t, 1H), 7.75-7.68 (m, 5H), 4.53 (m, 1H), 4.38 (m, 2H), 4.25 (m, 2H), 2.88 (s, 3H), 2.70 (m, 1H), 2.55 (m, 1H)

Example 92: Preparation of 1-(4-(4-chlorophenylsulfonyl)phthalazin-1-yl)-N-methylpyrrolidin-3-amine hydrochloride

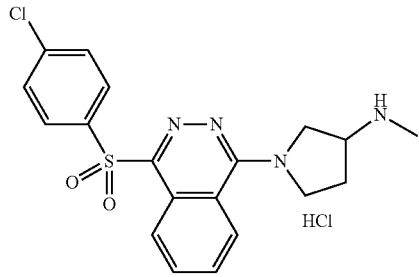 [SMILES: CNC1CCN(c2nnc(S(=O)(=O)c3ccc(Cl)cc3)c3ccccc23)C1 ; Cl]

Step 1) Preparation of tert-butyl (1-(4-((4-chlorophenyl)thio)phthalazin-1-yl) pyrrolidin-3-yl)(methyl)carbamate 1,4-Dichlorophthalazine (0.10 g, 0.50 mmol) and tert-butylmethyl (pyrrolidin-3-yl)carbamate (0.11 g, 0.50 mmol) were dissolved in n-butanol (3 mL). The mixture was stirred for 3 hours while maintaining an internal temperature at 70° C. to 80° C., and the termination of the reaction was confirmed by TLC. The reaction solution was concentrated under reduced pressure, and then the obtained residue was dissolved in N,N-dimethylformamide (2.0 mL), and 4-chlorobenzenethiol (0.09 g, 1.2 eq.) and $K_2CO_3$ (0.10 g, 1.5 eq.) were added at room temperature. The reaction was heated to 120° C. and stirred overnight. After confirming the disappearance of the starting material by TLC, the mixture was washed with ethyl acetate and filtered. The filtrate was concentrated under reduced pressure, and the resulting residue was separated by column chromatography (Hex:EA=3:1) to obtain the desired compound (0.03 g, yield 12.9%).

Step 2) Preparation of tert-butyl (1-(4-((4-chlorophenyl)sulfonyl)phthalazin-1-yl) pyrrolidin-3-yl)(methyl)carbamate The intermediate (0.03 g, 1.0 eq.) obtained in the above step 1 was dissolved in dichloromethane (2.0 mL) and then 3-chloroperbenzoic acid (mCPBA) (0.03 g, 2.5 eq.) was added thereto. The reaction solution was stirred at room temperature overnight, and then the disappearance of the starting material was confirmed by TLC. The reaction solution was concentrated under reduced pressure, and the resulting residue was separated and purified by preparative thin layer chromatography (Hex:EA=1:1) to obtain the desired compound (0.02 g, yield 62.3%).

Step 3) Preparation of 1-(4-(4-chlorophenylsulfonyl)phthalazin-1-yl)-N-methylpyrrolidin-3-amine hydrochloride To the intermediate (0.02 g, 1.0 eq.) obtained in the above step 2 was added 1N HCl in ethyl acetate (1.0 mL), and the mixture was stirred at room temperature overnight. After confirming that a white solid was formed, it was filtered to obtain the desired compound (0.20 g, yield 90.0%).

1H NMR (500 MHz, MeOD): 8.98 (d, 1H), 8.67 (m, 1H), 8.23 (m, 2H), 8.07 (d, 2H), 7.73 (d, 2H), 4.46 (m, 1H), 4.30 (m, 2H), 4.15 (m, 2H), 2.83 (s, 3H), 2.63 (m, 1H), 2.43 (m, 1H)

Example 93: Preparation of 1-(4-(4-chlorophenoxy)phthalazin-1-yl)-N-methylpyrrolidin-3-amine hydrochloride

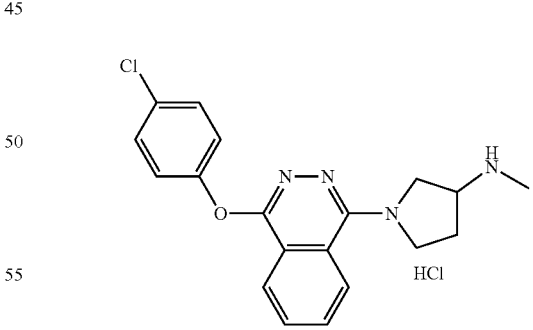

The intermediate was produced in the same manner as in the step 1 of Example 92 except that 4-chlorophenol was used instead of 4-chlorobenzenethiol. The desired compound was obtained in the same manner as in the step 3 of Example 92 except that the intermediate was used.

1H NMR (500 MHz, MeOD): 8.78 (d, 1H), 8.75 (d, 1H), 8.29 (t, 1H), 8.23 (t, 1H), 7.47 (d, 2H), 7.38 (d, 2H), 4.52 (m, 1H), 4.35 (m, 2H), 4.21 (m, 2H), 2.88 (s, 3H), 2.69 (m, 1H), 2.57 (m, 1H)

Hereinafter, the compound of Example 94 was produced in the same manner as in Example 93, except that reactants corresponding to the chemical structure of the compound to be produced were used.

Example 94: Preparation of 2-amino-1-(4-(4-(4-chlorophenoxy)phthalazin-1-yl)piperazin-1-yl)-2-methylpropan-1-one hydrochloride

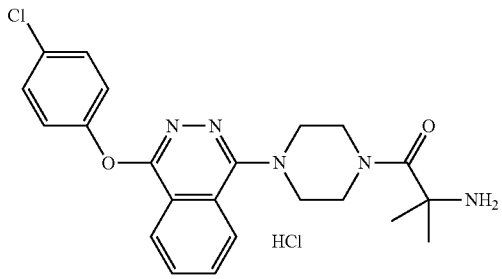 [SMILES: CC(C)(N)C(=O)N1CCN(c2nnc(Oc3ccc(Cl)cc3)c3ccccc23)CC1 ; Cl]

1H NMR (500 MHz, MeOD): 8.62 (d, 1H), 8.56 (d, 1H), 8.33 (t, 1H), 8.25 (t, 1H), 7.50 (d, 2H), 7.37 (d, 2H), 4.05 (m, 4H), 3.96 (m, 4H), 1.74 (s, 6H)

Example 95: Preparation of (S)-1-(4-chlorophenyl)-4-(pyrrolidin-3-yloxy)phthalazine hydrochloride

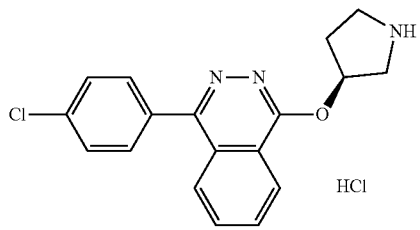 [SMILES: Clc1ccc(-c2nnc(O[C@H]3CCNC3)c3ccccc23)cc1 ; Cl]

1,4-Dichlorophthalazine (0.10 g, 0.50 mmol) was dissolved in dichloromethane (3 mL), and then NaOH (0.03 g, 0.75 mmol), tetrabutylammonium bromide (0.05 g, 0.15 mmol) and tert-butyl 3-hydroxypyrrolidine-1-carboxylate (0.11 g, 0.60 mmol) were added thereto. The mixture was stirred overnight at room temperature and the termination of the reaction was confirmed by TLC. Dichloromethane (5 mL) was added to the reaction solution, followed by washing with water. The organic layer was concentrated under reduced pressure and the resulting residue was separated by chromatography to obtain the desired intermediate (tert-butyl 3-(4-chlorophthalazin-1-yloxy) pyrrolidine-1-carboxylate). Thereafter, an intermediate was prepared in a similar manner to the reaction of the step 2 of Example 12, except that the above intermediate was used as a starting material. Finally, an elimination reaction of protective group was performed as in the step 3 of Example 31 to the desired compound.

1H NMR (500 MHz, MeOD): 8.77 (d, 1H), 8.46 (m, 1H), 8.32 (m, 2H), 7.90 (d, 2H), 7.83 (d, 2H), 3.95 (d, 1H), 3.85 (dd, 1H), 3.68 (m, 2H), 3.30 (m, 1H), 2.69 (m, 1H), 2.63 (m, 1H)

Hereinafter, the compound of Example 96 was produced in the same manner as in Example 95, except that reactants corresponding to the chemical structure of the compound to be produced were used.

Example 96: Preparation of 1-(4-chlorophenyl)-4-(piperidin-3-yloxy)phthalazine hydrochloride

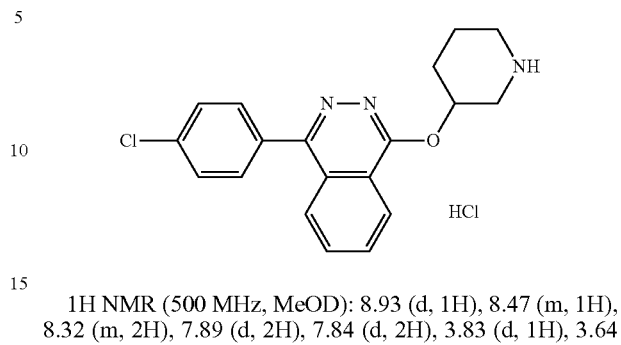

1H NMR (500 MHz, MeOD): 8.93 (d, 1H), 8.47 (m, 1H), 8.32 (m, 2H), 7.89 (d, 2H), 7.84 (d, 2H), 3.83 (d, 1H), 3.64 (d, 1H), 3.49 (d, 1H), 3.28 (m, 1H), 2.41 (m, 1H), 2.20 (m, 2H), 1.98 (d, 1H)

Example 97: Preparation of N-(4-chlorophenyl)-4-(3-(methylamino)pyrrolidin-1-yl)phthalazin-1-amine

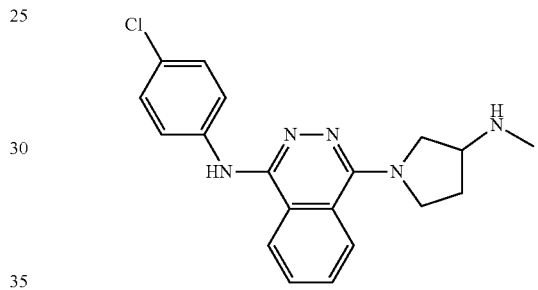

Step 1) Preparation of tert-butyl (1-(4-((4-chlorophenyl)amino) phthalazin-1-yl) pyrrolidin-3-yl) (methyl)carbamate 1,4-Dichlorophthalazine (1.0 g, 5.03 mmol) and tert-butylmethyl(pyrrolidin-3-yl)carbamate (1.11 g, 5.03 mmol) were dissolved in n-butanol (10 mL). The mixture was stirred for 3 hours while maintaining an internal temperature at 70° C. to 80° C., and the termination of the reaction was confirmed by TLC. The reaction solution was concentrated under reduced pressure, and then the obtained residue was dissolved in 1,4-dioxane (3.0 mL), and then 4-chloroaniline (0.02 g, 1.2 eq.), rac-BINAP (0.22 g, 0.2 eq.), palladium(II) acetate (0.03 g, 0.1 eq.) and cesium carbonate (1.10 g, 2 eq.) were added thereto. The reaction solution was reacted at 120° C. for 30 minutes under microwave. After confirming the disappearance of the starting material by TLC, the mixture was washed with ethyl acetate and filtered. The filtrate was concentrated under reduced pressure, and the resulting residue was separated and purified by preparative thin layer chromathography (Hex:EA=1:1) to obtain the desired intermediate tert-butyl (1-(4-(4-(chlorophenyl) amino)phthalazine-yl)pyrrolidin-3-yl) (methyl)carbamate (0.02 g, yield 32.2%).

Step 2) Preparation of N-(4-chlorophenyl)-4-(3-(methylamino)pyrrolidin-1-yl) phthalazin-1-amine To the intermediate (0.02 g, 1.0 eq.) obtained in the above step 1 was added 1N HCl in ethyl acetate (1.0 mL), and the mixture was stirred at room temperature overnight. After confirming that a white solid was formed, it was filtered to obtain the desired compound (0.10 g, yield 58.2%).

1H NMR (500 MHz, MeOD): 8.33 (t, 2H), 7.94 (d, 2H), 7.64 (d, 2H), 7.28 (d, 2H), 3.83 (m, 2H), 3.69 (m, 1H), 3.66 (m, 2H), 2.63 (s, 3H), 2.38 (m, 1H), 2.03 (m, 1H)

Example 98: Preparation of 1-(4-(4-chlorobenzyl) phthalazin-1-yl)-N-methylpyrrolidin-3-amine hydrochloride

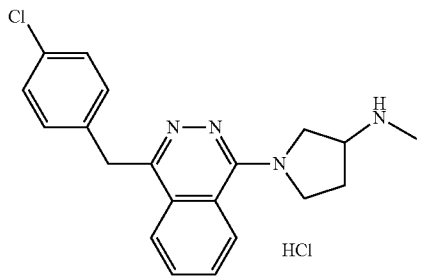 [SMILES: CNC1CCN(c2nnc(Cc3ccc(Cl)cc3)c3ccccc23)C1 ; Cl]

Step 1) Preparation of 4-(4-chlorobenzyl)phthalazin-1(2H)-one

Isobenzofuran-1(3H)-one (0.50 g, 1.0 eq.) was dissolved in methanol (2.0 mL) and ethyl acetate (10.0 mL) and then 4-chlorobenzaldehyde (0.52 g, 1.0 eq.) was added thereto. NaOH (0.60 g, 4.0 eq.) was dissolved in methanol (8.0 mL) and added to the reaction solution. The mixture was then stirred overnight at 80° C. After confirming the disappearance of the starting material by TLC, the reaction solution was concentrated under reduced pressure. Water and ethyl acetate were added to the obtained residue, and the extracted organic layer was dried over anhydrous magnesium sulfate and concentrated under reduced pressure. Hydrazine hydrate (20.0 mL) was added to the obtained residue, followed by stirring overnight at 80° C. The reaction solution was cooled at room temperature and concentrated under reduced pressure. Ethanol (10.0 mL) was added to the obtained residue and cooled to 0° C. using ice. After confirming that a transparent red solid was crystallized, it was filtered to obtain the desired intermediate 4-(4-chlorobenzyl)phthalazin-1(2H)-one (0.25 g, yield 24.8%).

Step 2) Preparation of 1-chloro-4-(4-chlorobenzyl)phthalazine

The intermediate (0.11 g, 1.0 eq.) obtained in the above step 1 was dissolved in acetonitrile (2.0 mL), and then phosphoryl chloride (2.0 mL) and N,N-dimethylformamide (some drops) were added thereto. The reaction solution was heated to 100° C. and allowed to react for 4 hours. After confirming the disappearance of the starting material by TLC, water and saturated sodium hydrogen carbonate aqueous solution were added. After confirming that a red solid was crystallized, it was filtered to obtain the desired intermediate 1-chloro-4-(4-chlorobenzyl)phthalazine (0.08 g, yield 68.1%).

Step 3) Preparation of 1-(4-(4-chlorobenzyl)phthalazin-1-yl)-N-methylpyrrolidin-3-amine hydrochloride The intermediate (0.08 g, 0.28 mmol) obtained in the above step 2, triethylamine (0.08 mL, 0.56 mmol) and tert-butylmethyl (pyrrolidin-3-yl) carbamate (0.06 g, 0.28 mmol) were dissolved in n-butanol (5 mL). The mixture was stirred overnight while maintaining an internal temperature at 70° C. to 80° C., and the termination of the reaction was confirmed by TLC. The reaction solution was concentrated under reduced pressure, and then water and ethyl acetate were added to the obtained residue. The extracted organic layer was dried over anhydrous magnesium sulfate and then concentrated under reduced pressure. To the obtained residue was added 1N HCl in ethyl acetate (2.0 mL), and the mixture was stirred overnight at room temperature. After confirming that a white solid was formed, it was filtered to obtain the desired compound (0.10 g, yield 10.1%, 2-step).

1H NMR (500 MHz, MeOD): 8.64 (br, 1H), 8.29 (d, 1H), 8.09 (m, 2H), 7.31 (m, 4H), 4.59 (s, 2H), 4.41 (br, 1H), 4.30 (br, 2H), 4.13 (br, 2H), 2.84 (s, 3H), 2.63 (m, 1H), 2.47 (m, 1H), 2.15 (s, 3H)

Hereinafter, the compounds of Examples 99 to 108 were each produced in the same manner as in Example 31, except that reactants corresponding to the chemical structure of the compound to be produced were used Example 99: Preparation of 3-(4-(4-(2-amino-2-methylpropanoyl)piperazin-1-yl)phthalazin-1-yl) benzoic acid hydrochloride

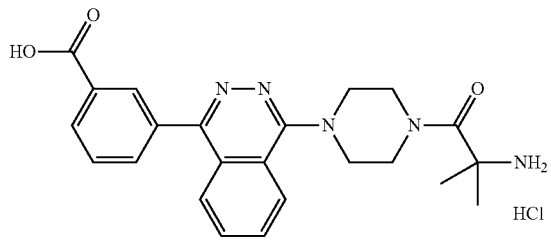 [SMILES: CC(C)(N)C(=O)N1CCN(c2nnc(-c3cccc(C(=O)O)c3)c3ccccc23)CC1 ; Cl]

1H NMR (500 MHz, MeOD): 8.59 (d, 1H), 8.43 (s, 1H), 8.40 (d, 1H), 8.33 (t, 1H), 8.21 (m, 2H), 8.02 (d, 1H), 7.86 (d, 1H), 4.06 (m, 4H), 3.95 (m, 4H), 1.77 (s, 6H)

Example 100: Preparation of 2-amino-2-methyl-1-(4-(4-(4-morpholinophenyl)phthalazin-1-yl)piperazin-1-yl)propan-1-one hydrochloride

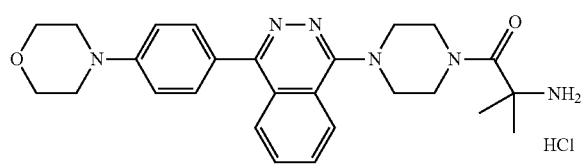 [SMILES: CC(C)(N)C(=O)N1CCN(c2nnc(-c3ccc(N4CCOCC4)cc3)c3ccccc23)CC1 ; Cl]

1H NMR (500 MHz, MeOD): 8.52 (d, 1H), 8.43 (d, 1H), 8.34 (t, 1H), 8.22 (t, 1H), 7.73 (d, 2H), 7.29 (d, 2H), 4.02 (m, 4H), 3.88 (m, 4H), 3.77 (m, 4H), 3.42 (m, 4H), 1.75 (s, 6H)

Example 101: Preparation of 2-amino-2-methyl-1-(4-(4-(4-(methylsulfonyl)phenyl)phthalazin-1-yl)piperazin-1-yl)propan-1-one hydrochloride

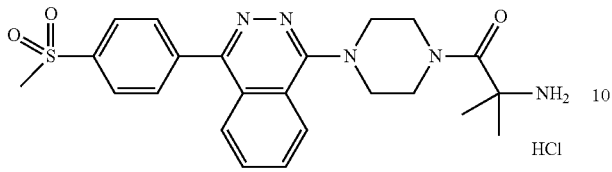

1H NMR (500 MHz, MeOD): 8.61 (d, 1H), 8.27 (m, 3H), 8.22 (t, 1H), 8.17 (d, 1H), 8.03 (d, 2H), 4.08-4.01 (m, 8H), 1.77 (s, 6H)

Example 102: Preparation of 2-amino-2-methyl-1-(4-(4-(4-(trifluoromethyl)phenyl)phthalazin-1-yl)piperazin-1-yl)propan-1-one hydrochloride

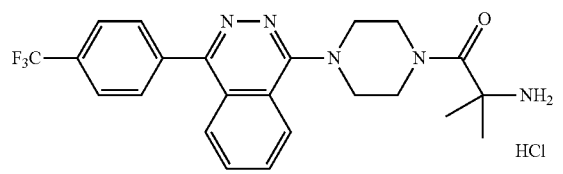 [SMILES: CC(C)(N)C(=O)N1CCN(c2nnc(-c3ccc(C(F)(F)F)cc3)c3ccccc23)CC1 ; Cl]

1H NMR (500 MHz, MeOD): 8.61 (d, 1H), 8.30 (t, 1H), 8.21 (t, 1H), 8.17 (d, 1H), 8.01 (m, 4H), 4.07-4.01 (m, 8H), 1.77 (s, 6H)

Example 103: Preparation of 2-amino-2-methyl-1-(4-(4-(4-(trifluoromethoxy)phenyl)phthalazin-1-yl)piperazin-1-yl)propan-1-one hydrochloride

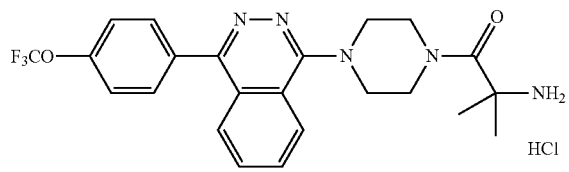 [SMILES: CC(C)(N)C(=O)N1CCN(c2nnc(-c3ccc(OC(F)(F)F)cc3)c3ccccc23)CC1 ; Cl]

1H NMR (500 MHz, MeOD): 8.60 (d, 1H), 8.32 (m, 1H), 8.22 (m, 2H), 7.92 (d, 2H), 7.63 (d, 2H), 4.06 (m, 4H), 3.95 (m, 4H), 1.77 (s, 6H)

Example 104: Preparation of 3-(4-(4-(4-(2-amino-2-methylpropanoyl)piperazin-1-yl)phthalazin-1-yl)phenyl)propanoic acid hydrochloride

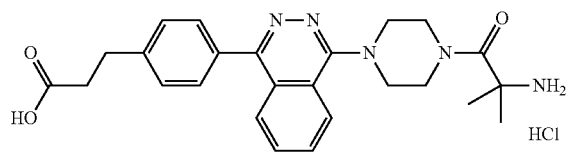 [SMILES: CC(C)(N)C(=O)N1CCN(c2nnc(-c3ccc(CCC(=O)O)cc3)c3ccccc23)CC1 ; Cl]

1H NMR (500 MHz, MeOD): 8.54 (d, 1H), 8.29 (t, 1H), 8.26 (d, 1H), 8.21 (t, 1H), 7.73 (d, 2H), 7.65 (d, 2H), 4.03 (br, 4H), 3.83 (br, 4H), 3.11 (m, 2H), 2.75 (m, 2H), 1.75 (s, 6H)

Example 105: Preparation of 4-(4-(4-(2-amino-2-methylpropanoyl)piperazin-1-yl)phthalazin-1-yl)benzoic acid hydrochloride

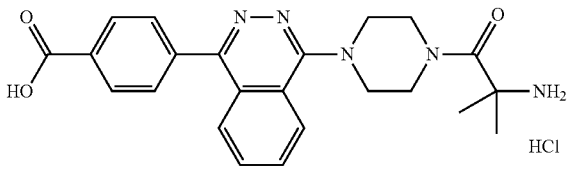 [SMILES: CC(C)(N)C(=O)N1CCN(c2nnc(-c3ccc(C(=O)O)cc3)c3ccccc23)CC1 ; Cl]

1H NMR (500 MHz, MeOD): 8.57 (d, 1H), 8.34 (d, 2H), 8.32 (m, 1H), 8.22 (m, 2H), 7.90 (d, 2H), 4.05 (br, 4H), 3.94 (br, 4H), 1.76 (s, 6H)

Example 106: Preparation of 2-amino-2-methyl-1-(4-(4-(4-(4-methylpiperazine-1-carbonyl)phenyl)phthalazin-1-yl)piperazin-1-yl)propan-1-one dihydrochloride

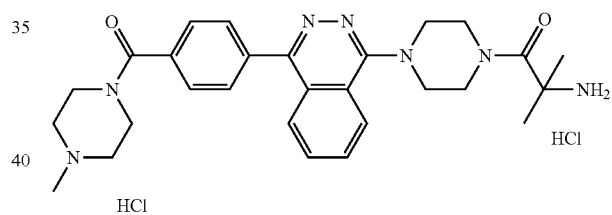

1H NMR (500 MHz, MeOD): 8.59 (d, 1H), 8.32 (t, 1H), 8.23 (m, 2H), 7.92 (d, 2H), 7.83 (d, 2H), 4.07 (m, 4H), 3.96 (m, 4H), 3.61 (m, 4H), 2.99 (s, 3H), 1.76 (s, 6H)

Example 107: Preparation of 2-amino-2-methyl-1-(4-(4-(4-(piperidin-1-ylsulfonyl)phenyl)phthalazin-1-yl)piperazin-1-yl)propan-1-one hydrochloride

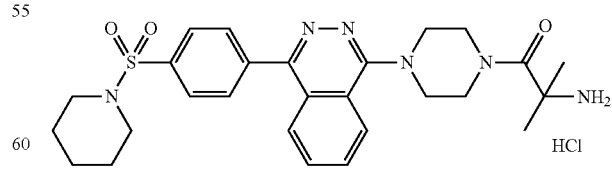

1H NMR (500 MHz, MeOD): 8.56 (d, 1H), 8.28 (t, 1H), 8.19 (m, 2H), 8.07 (d, 2H), 8.00 (d, 2H), 4.06 (br, 4H), 3.95 (br, 4H), 3.11 (m, 4H), 1.76 (s, 6H), 1.68 (m, 4H), 1.50 (m, 2H)

Example 108: Preparation of 2-amino-2-methyl-1-(4-(4-(3-(piperazin-1-ylsulfonyl)phenyl)phthalazin-1-yl)piperazin-1-yl)propan-1-one dihydrochloride

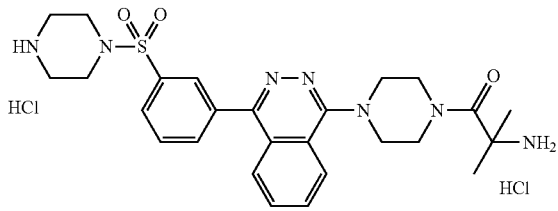 [SMILES: Cl ; CC(C)(N)C(=O)N1CCN(c2nnc(-c3cccc(S(=O)(=O)N4CCNCC4)c3)c3ccccc23)CC1 ; Cl]

1H NMR (500 MHz, MeOD): 8.56 (d, 1H), 8.27 (t, 1H), 8.23 (m, 2H), 8.17 (m, 1H), 8.11 (d, 2H), 7.99 (t, 1H), 4.08 (m, 4H), 3.97 (m, 4H), 3.42 (m, 4H), 3.36 (m, 4H), 1.76 (s, 6H)

Experimental Example: Evaluation of the Ability to Inhibit TNF-α Secretion by hResistin

Using THP-1 (human monocyte) cell line and ELISA system, the abilities to inhibit TNF-α secretion by hResistin ($IC_{50}$) were evaluated for the compounds prepared in the above examples. The compounds target hResistin, and the abilities of the compounds to inhibit TNF-α secretion by human recombinant Resistin in human monocyte (THP-1) were evaluated. The abilities to inhibit TNF-α secretion were assessed by ELISA quantifying the amount of antibody with the enzyme as a marker using an antigen-antibody reaction.

Specifically, the cultured cells were spun down at 1,500 rpm for 2 minutes, the supernatant was removed and then the cells were re-suspended in 10 mL of complete RPMI-1640 medium. After counting the number of cells using Luna™ Automated Cell Counter, cells were plated into 96-well assay plates at 50 μL per well. The cells cultured for 24 hours were treated with the test substances in accordance with the concentration for 1 hour, and then the supernatant was collected and subjected to ELISA assay. In the ELISA assay, the absorbance at 450 nm ($OD_{450}$ nm) was measured using Flexstation 3. The ability of each test substance to inhibit TNF-α secretion ($IC_{50}$) and its inhibition at a concentration of 5 uM are shown in Table 1 below.

TABLE 1

| Ex. No. | $IC_{50}$ (μM) | Inhibition (5 μM, %) |
| --- | --- | --- |
| 1 | 1 | — |
| 2 | 5 | — |
| 4 | 1.6 | 40.4 |
| 8 | — | 54.4 |
| 9 | 3.7 | — |
| 10 | 1.2 | — |
| 34 | 3 | 64.9 |
| 36 | 2.5 | 75.8 |
| 37 | — | 52.9 |
| 38 | 7.9 | 69.5 |
| 43 | 1.3 | 84.4 |
| 44 | — | 50.5 |
| 45 | 1.6 | 77.6 |
| 46 | 0.3 | 97.8 |
| 47 | 0.7 | 87.1 |
| 50 | — | 54 |
| 51 | 0.8 | 88.2 |
| 53 | — | 8.7 |
| 54 | 1.9 | 70.0 |
| 55 | — | 13.1 |
| 56 | — | 26.2 |
| 57 | 1.0 | 92.8 |
| 58 | 2.9 | 77.3 |
| 59 | — | 60.3 |
| 60 | 1.9 | 91.2 |
| 61 | — | 21.2 |
| 62 | — | 24.8 |
| 63 | — | 53.6 |
| 64 | — | 23.9 |
| 65 | — | 2.4 |
| 67 | — | 38.9 |
| 69 | — | 16.1 |
| 70 | — | 61.4 |
| 71 | — | 42.2 |
| 72 | — | 72.2 |
| 73 | — | 53.6 |
| 74 | — | 38.7 |
| 75 | — | 30.9 |
| 76 | — | 28.9 |
| 77 | — | 46.7 |
| 78 | — | 81.3 |
| 79 | — | 65.4 |
| 80 | — | 69.9 |
| 81 | — | 48.1 |
| 82 | — | 50.0 |
| 84 | — | 12.6 |
| 85 | 5.4 | 45.3 |
| 86 | 18.0 | — |
| 87 | 1.7 | — |
| 88 | 0.9 | — |
| 89 | 1.8 | 77.9 |
| 90 | 0.9 | 86.7 |
| 91 | 0.6 | 76.6 |
| 93 | 1.9 | 67.6 |
| 94 | — | 29.9 |
| 95 | 2.3 | 64.0 |
| 96 | — | 58.9 |
| 97 | — | 26.9 |
| 98 | — | 3.9 |
| 102 | — | 37.0 |
| 103 | — | 32.0 |
| 104 | — | 0.6 |

What is claimed is:

1. A compound represented by the following Chemical Formula 1, or a pharmaceutically acceptable salt thereof:

[Chemical Formula 1]

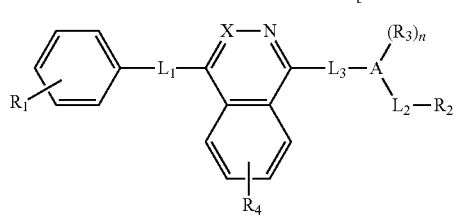

in Chemical Formula 1,

X is N, $L_1$ is a single bond, $C_{1-4}$ alkylene, $C_{2-4}$ alkenylene, NH, O, or $SO_2$, $L_3$ is a single bond, $R_1$ is hydrogen, $C_{1-4}$ alkyl, $C_{1-4}$ alkyl substituted with carboxy group, $C_{1-4}$ haloalkyl, $C_{1-4}$ alkoxy, $C_{1-4}$ haloalkoxy, halogen, cyano, nitro, 4-methylpiperazin- 1-carbonyl, carboxy, morpholino, ($C_{1-4}$ alkyl)sulfonyl, (piperidinyl)sulfonyl, or (piperazinyl)sulfonyl, $R_3$ is hydrogen, or $C_{1-4}$ alkyl, $R_4$ is hydrogen, or halogen, n is 1 or 2, and $A-L_2-R_2$ is represented by the following formula 1':

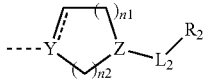

[Chemical Formula 1']

in Chemical Formula 1',

Y is N, ⫽ is a single bond,

Z is CH, or N, n1 is 1, n2 is 1 or 2, $L_2$ is NH, and $R_2$ is $C_{1-4}$ alkyl unsubstituted or substituted with amino; $C_{3-6}$ cycloalkyl; amino; N($C_{1-4}$ alkyl)$_2$; hydroxy; morpholino; or pyrrolidinyl.

2. The compound or a pharmaceutically acceptable salt thereof according to claim 1, wherein $L_1$ is a single bond, —$CH_2$—, —CH=CH—, —$CH_2$—CH=CH—, NH, O, or $SO_2$.

3. The compound or a pharmaceutically acceptable salt thereof according to claim 1, wherein $R_1$ is hydrogen, methyl, ethyl substituted with carboxy group, trifluoromethyl, methoxy, trifluoromethoxy, fluoro, chloro, cyano, nitro, 4-methylpiperazine-1-carbonyl, carboxy, morpholino, methylsulfonyl, (piperidin-1-yl)sulfonyl, or (piperazin-1-yl)sulfonyl.

4. The compound or a pharmaceutically acceptable salt thereof according to claim 1, wherein $R_2$ is methyl, ethyl, propyl, isopropyl, butyl, isobutyl, isopentyl, cyclopropyl, cyclobutyl, cyclopentyl, amino, dimethylamino, hydroxyl, morpholino, or pyrrolidinyl.

5. The compound or a pharmaceutically acceptable salt thereof according to claim 1, wherein the compound represented by the Chemical Formula 1 is any one selected from the group consisting of:

1) 1-(4-(4-chlorophenyl)phthalazin-1-yl)-N-methylpyrrolidin-3-amine hydrochloride, 2) 1-(4-(4-chlorophenyl)phthalazin-1-yl)-N-ethylpyrrolidin-3-amine, 3) (R)-1-(4-(4-chlorophenyl)phthalazin-1-yl)-N-methylpiperidin-3-amine, 4) 1-(7-chloro-4-(4-chlorophenyl)phthalazin-1-yl)-N-methylpyrrolidin-3-amine, 5) 1-(6-chloro-4-(4-chlorophenyl)phthalazin-1-yl)-N-methylpyrrolidin-3-amine, 6) 1-(4-(4-chlorophenyl)-6-fluorophthalazin-1-yl)-N-methylpyrrolidin-3-amine, 7) 1-(4-(4-chlorophenoxy)phthalazin-1-yl)-N-methylpyrrolidin-3-amine, 8) N-(4-chlorophenyl)-4-(3-(methylamino)pyrrolidin-1-yl)phthalazin-1-amine, and 9) 1-(4-(4-chlorobenzyl)phthalazin-1-yl)-N-methylpyrrolidin-3-amine.

6. A pharmaceutical composition for preventing or treating cardiovascular diseases, comprising the compound according to claim 1 or a pharmaceutically acceptable salt thereof.

\* \* \* \* \*